(12) United States Patent
Hubbard et al.

(10) Patent No.: US 6,338,820 B1
(45) Date of Patent: *Jan. 15, 2002

(54) APPARATUS FOR PERFORMING ASSAYS AT REACTION SITES

(75) Inventors: Allyn Hubbard, Medfield; Samesh Kale, Allston, both of MA (US); Scott A. Rollins, Oxford, CT (US); Jeremy P. Springhorn, Guilford, CT (US); Stephen P. Squinto, Bethany, CT (US)

(73) Assignee: Alexion Pharmaceuticals, Inc., Cheshire, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/134,141

(22) Filed: Aug. 14, 1998

Related U.S. Application Data

(60) Provisional application No. 60/055,792, filed on Aug. 15, 1997.

(51) Int. Cl.[7] ......................... G01N 35/00; G01N 35/10
(52) U.S. Cl. ........................... 422/64; 422/63; 422/65; 422/67; 422/72; 422/100; 436/43; 436/45; 436/50; 436/164; 436/165; 436/180
(58) Field of Search ............................. 422/63, 65, 64, 422/67, 72, 100; 436/43, 45, 50, 164, 165, 180; 435/287.2, 288.4, 288.5

(56) References Cited

U.S. PATENT DOCUMENTS

| | | |
|---|---|---|
| 3,679,367 A | 7/1972 | Negersmith et al. |
| 4,258,647 A | 3/1981 | Pohl et al. |

(List continued on next page.)

FOREIGN PATENT DOCUMENTS

| | | |
|---|---|---|
| EP | 0305210 | 3/1989 |
| EP | 0322657 | 5/1989 |

(List continued on next page.)

OTHER PUBLICATIONS

John A. Wright, et al., Towards a Functional Mems Neurowell by Physiological Experimentation, DSC—vol. 59, Microelectromechanical Systems (MEMS) ASME (1996).

(List continued on next page.)

Primary Examiner—Jill Warden
Assistant Examiner—Kathryn Bex
(74) Attorney, Agent, or Firm—Mintz, Levin, Cohn, Ferris, Glovsky & Popeo, P.C.; Ivor R. Elrifi; Brian P. Hopkins

(57) ABSTRACT

An apparatus for performing a assays includes an axially rotatable substrate including a plurality of layers of a semiconductor material and numerous radially-arrayed reaction sites. The apparatus further includes a rotary stepper motor which rotates the substrate at an adjustable and substantially continuous speed and controls the rotation of the substrate by adjusting the speed and a direction of rotation. In addition, the apparatus includes a dual function head which has a fluid dispenser that has a fluid dispenser outlet and delivers a fluid to a reaction site and also has a readout device that has a sensor which receives an identifying signal from the reaction site on the substrate or scans the substrate to read identifying marks at the reaction site. Moreover, the apparatus may be aligned by a computer having a memory for storing a start location for the dispenser outlet on the substrate and additional electronics. The computer provides movement signals to the rotary stepper motor and a linear stepper motor on which the dispenser outlet is mounted, whereby the motors align the dual function head over the substrate, such that the dispenser outlet is aligned over the reaction site.

52 Claims, 20 Drawing Sheets

U.S. PATENT DOCUMENTS

| | | | |
|---|---|---|---|
| 4,279,862 | A | 7/1981 | Bretaudiere et al. |
| 4,381,291 | A | 4/1983 | Ekins |
| 4,495,149 | A | 1/1985 | Iwata et al. |
| 4,515,889 | A | 5/1985 | Klose et al. |
| 4,676,952 | A | 6/1987 | Edelmann et al. |
| 4,745,072 | A | 5/1988 | Ekins et al. |
| 4,940,527 | A | 7/1990 | Kazlauskas et al. |
| 5,006,749 | A | 4/1991 | White |
| 5,160,702 | A | 11/1992 | Kopf-Sill et al. |
| 5,171,533 | A * | 12/1992 | Fine et al. ............... 422/72 |
| 5,171,695 | A | 12/1992 | Ekins |
| 5,173,262 | A | 12/1992 | Burtis et al. |
| 5,242,803 | A | 9/1993 | Burtis et al. |
| 5,252,294 | A | 10/1993 | Kroy et al. |
| 5,304,487 | A | 4/1994 | Wilding et al. |
| 5,368,704 | A | 11/1994 | Madou et al. |
| 5,409,665 | A | 4/1995 | Burd |
| 5,413,732 | A | 5/1995 | Buhl et al. |
| 5,449,621 | A * | 9/1995 | Klein ..................... 436/45 |
| 5,472,603 | A | 12/1995 | Schembri |
| 5,532,128 | A | 7/1996 | Eggers et al. |
| 5,599,502 | A * | 2/1997 | Miyazaki et al. ....... 422/82.01 |
| 5,627,041 | A | 5/1997 | Shartle |
| 5,639,428 | A * | 6/1997 | Cottingham ............ 422/112 |
| 5,935,785 | A * | 8/1999 | Reber et al. ............. 435/6 |
| 6,013,513 | A * | 1/2000 | Reber et al. .......... 435/288.5 |

FOREIGN PATENT DOCUMENTS

| | | |
|---|---|---|
| EP | 0410645 | 1/1991 |
| EP | 0417305 | 3/1991 |
| EP | 0523522 | 1/1993 |
| EP | 0616218 | 9/1994 |
| JP | 3245049 | 10/1991 |
| WO | 9322058 | 11/1993 |
| WO | 9631782 | 10/1996 |
| WO | 9721090 | 6/1997 |

OTHER PUBLICATIONS

Carol T. Schembri, et al., Portable Simultaneous Multiple Analyte Whole–Blood Analyzer for Point–of–Care Testing, Clinical Chemistry 1665–1670, vol. 38, No. 9 (1992).

European Search Report mailed Dec. 12, 1998.

Philipe Arquint et al., Micromachined Analyzers on a Silicon Chip, Clinical Chemistry, 1805–1809, vol. 40, No. 9 (1994).

Gary Whomas and Wil Ophey, Optical Recording, Physics World, 36–41 (1990).

Schematic Drawing, Sony KSS36361A Optical Pickup Organization (Date Unknown).

Beth Burkstrand, Breakthrough Reported on Gene–Reading 'Biochip', E03 (Jun. 30, 1998) <http://www.washingtonpost.com/wp–srv/WPlate/1998–06/30/0981–063098–idx.html>.

Motorola, Packard to Make 'Biochips' (Jun. 29, 1998) <http://washingtonpost.com/wp–srv/digest/tech2.htm>.

Introducing the BioChip Arrayer™ (May 15, 1998) <http://www.packardinst.com/pr/pr598–1.htm>.

Motorola, Packard Instrument Co. and Argonne to Develop Advanced Biochip Technology (Jun. 29, 1998) <http://www.packardinst.com/pr/pr698–3.htm>.

New Advanced Tools to Decode the Human Genome Introduced by Packard Instrument Company (Jun. 29, 1998) <http://www.packardinst.com/pr/pr698–4.htm>.

* cited by examiner

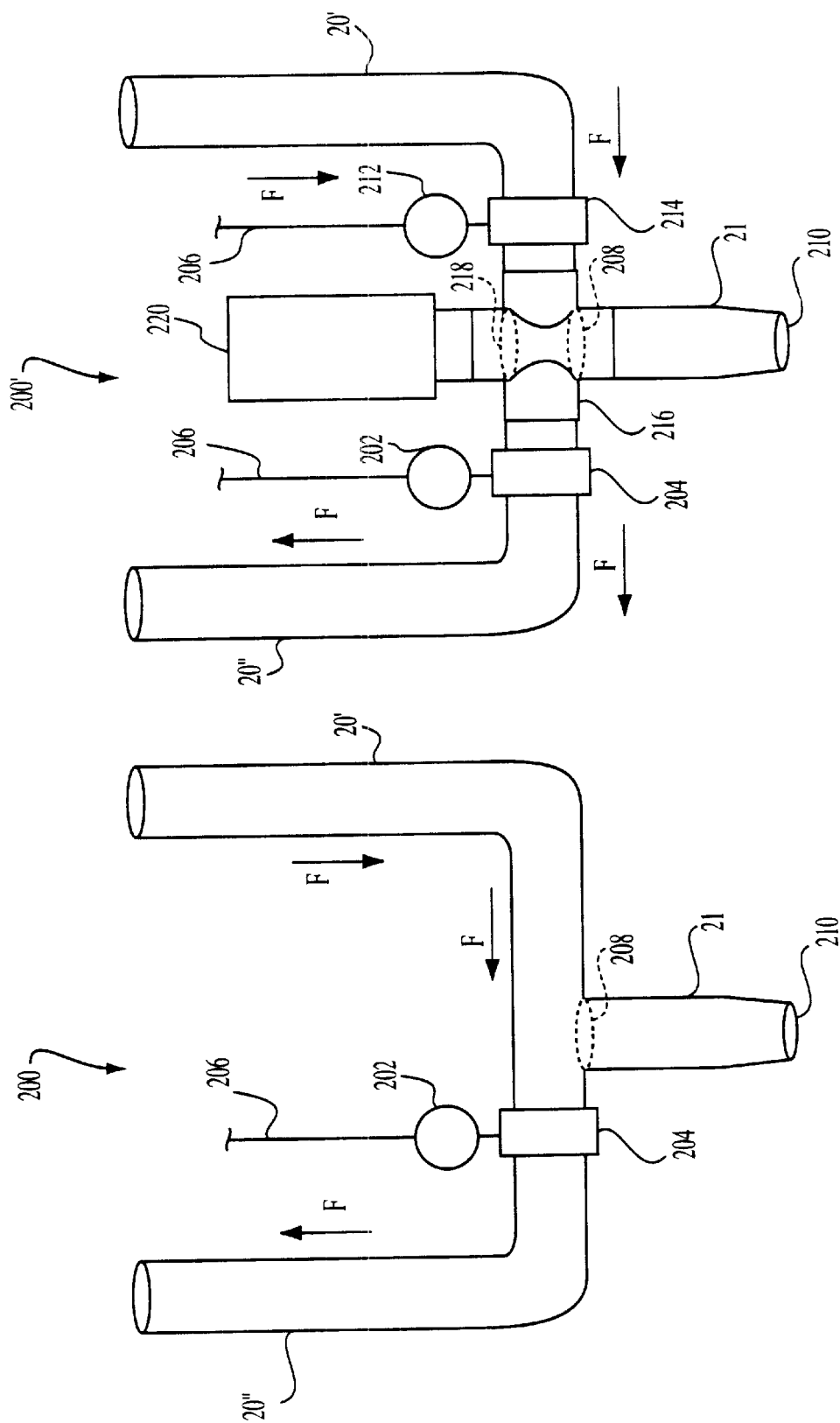

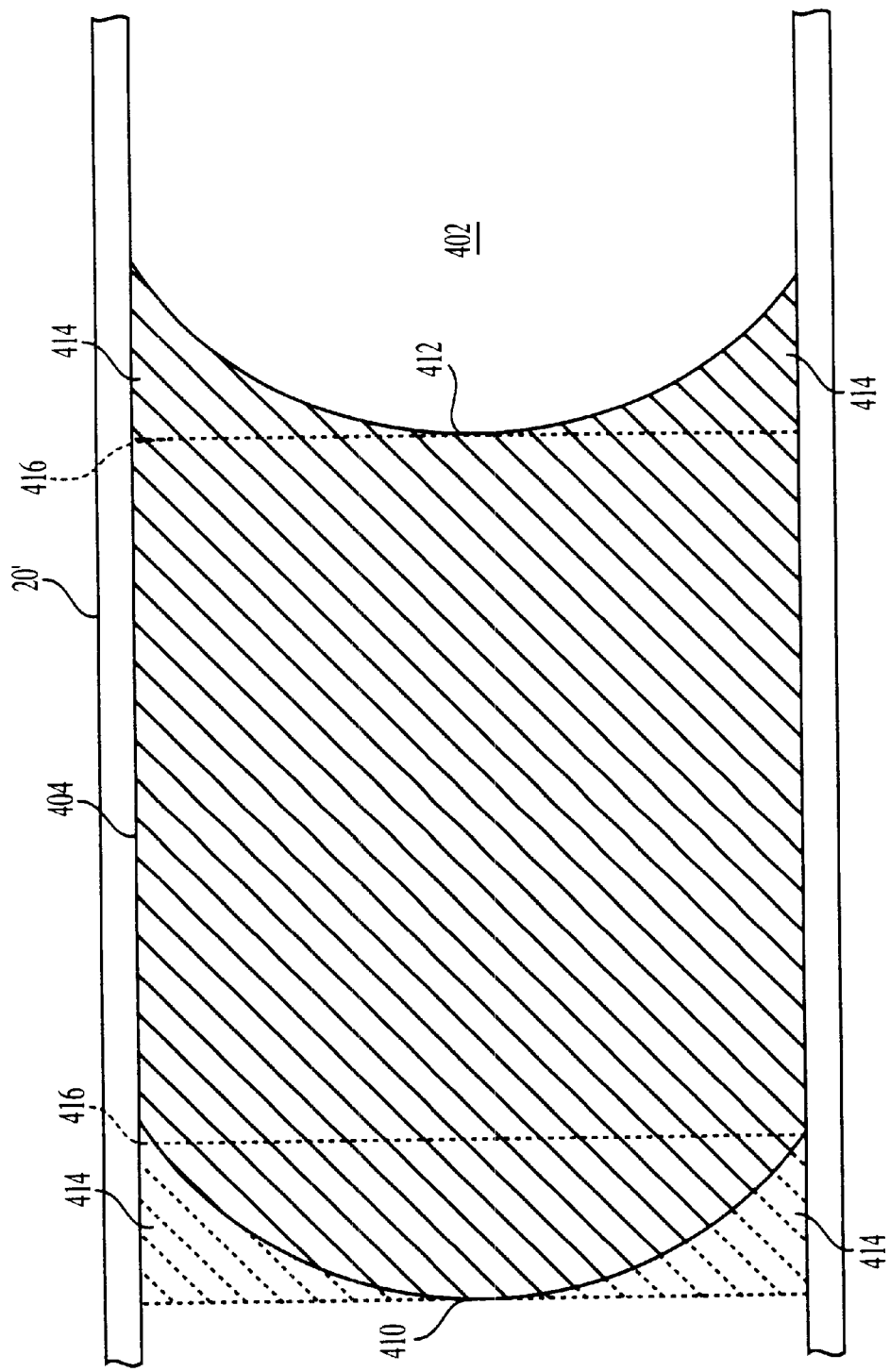

APPARATUS FOR PERFORMING ASSAYS AT REACTION SITES

This Application claim benefit to provisional Application No. 60/055,792 Aug. 15, 1997.

BACKGROUND OF THE INVENTION

1. Field of the Invention

The invention generally relates to apparatus for performing assays, such as chemical assays and biochemical reactions, or the like, at reaction sites on a substrate. In particular, the invention relates to apparatus for performing assays, such as chemical assays and biochemical reactions by delivering a selected aliquot or selected aliquots to a reaction site or sites on a substrate that may include a plurality of layers of semiconductor material.

2. Description of the Related Art

Until the relatively recent advent of combinatorial chemistry and genetic research spawned the need for high-throughput analyzing and screening techniques, researchers performed such assays using vials, tubes, and beakers. However, with ever more substances available via synthesis or via combinatorial techniques for testing, the need has arisen to test the possible role of thousands, or even millions of substances, in comparable numbers of possible reactions. Miniaturization has been identified as a promising path to more efficient, e.g., less expensive, chemical, and in particular, drug, analysis and screening. Discussions of various aspects of such analysis and screening techniques are found in J. D. Devlin, ed., *High Throughput Screening: The Discovery of Bioactive Substances* (Marcel Dekker, Inc., New York, 1997); which is incorporated herein by reference to more fully describe the state of the art to which the present invention pertains.

Miniaturization apparatus may be broadly classified into at least two categories. A first category involves the placement of chemical substances in small amounts in sites formed on glass or a similar substrate. Micro-chemistry includes processes carried out in small volumes, e.g., between nanoliter and microliter aliquots, whereby reaction times may be shortened significantly over those conducted in reaction vessels holding on the order a fraction of a milliliter, as currently achievable by a lab technician working "by hand." In addition to microchemical testing, levels of gene expression may be tested on a large scale.

An example of this first category is the development of microplate technology in which a glass substrate may include site densities of about 10,000 sites. This technology may include the use of complex micro-robotics or the adaptation of ink-jet technology to apply chemical and biochemical substances to chosen sites on the substrates. Frequently, at least one of the reactants in a chemical assay to be performed is chemically linked to or otherwise immobilized at the reaction site. This is done, so that fluids may be added to and removed from the reaction site without removing at least one intermediate or end product of the reaction, which intermediate or end product(s) is (are) to be retained at the reaction site, so that the outcome of the chemical assay may thereby be detected.

Orchid Biocomputer ("Orchid") of Princeton, N.J., USA, has indicated that it plans to create a credit-card sized glass chip with 10,368 sites. See M. Leach, *Update: Discovery on a Credit Card?*, DRUG DISCOVERY TODAY, 253–4 (Vol. 2, No. 7 (July 1997). For example, each site may cover an area of 100 $\mu m^2$ and may contain less than 1 $\mu l$ in volume. The chip is a glass sandwich formed from individual chip layers, which then may be glued together to form tubes to move substances between sites. Such tubes are formed in this device by cutting, e.g., etching, trenches or grooves in a first layer and then sandwiching the trenches under a second layer.

A second category of miniaturization apparatus employs silicon in some functional, e.g., electrical or mechanical, modality as the substrate, and chemicals then are tested on the substrate. In some cases, micro-robotics or micro-chemistry, or both, may be employed with such substrates. For example, Orchid's chip may employ microfluidic pumps, e.g., electronic pumps having no moving parts, to move substances between sites. Nanogen, Inc. also has developed a microelectronic device for handling low-dilutions of charged molecules. However, unlike Orchid, which may use electrokinetic pressure pumping, the Nanogen device employs electrophoresis as a motive agent to analyze chemical reactions acting over the surface of the silicon substrate at about twenty-five reaction sites. Electrokinetic pressure pumping has been described as a combination of electrophoresis and electro-osmosis.

Other research has addressed developing products which employ in-place silicon substrates or devices for chemical testing that include either electrical or micro-mechanical technologies, or both. For example, Synteni, Inc. has developed a process which simultaneously measures the expression of thousands of genes using microscopic cDNA portions placed on a substrate. Synteni also has developed a companion reader that uses two-color fluorescence hybridization detection. Genometrix, Inc. also employs a fluorescence analysis technique that appears similar in concept to the Synteni's process, but carries out the reactions on miniature scale, i.e., on a film that eventually fits over the surface of a reaction reader. Such a reader is manufactured from a silicon chip or wafer modified to function as a photodetector, such as a charge-coupled device (CCD).

Fluorescence generated on the film produces a photocurrent, which provides an electrical charge to a CCD site, and which subsequently may be gated out for analysis, in a manner analogous to the function of a CCD detector array in a digital camera. Thus, known digitizing technology may be combined with the placement of an arrays of chemicals on the surface of a plastic film. The plastic reaction array film may be fitted over the surface of silicon chip or wafer that acts as the reader and when ultra-violet light is flooded over the film surface, fluorescence is elicited from the chemical reaction sites. Each reaction site on the film is aligned with an analyzing site on the reader, and, therefore, a coordinate on the reader corresponds to a reaction site in the chemical array.

Nevertheless, previous attempts to achieve high-throughput analyzing and screening techniques for chemical reactions have required complex operations using combinations of films and substrates or complex robotics for the precise placement of fluids carrying chemical compositions, or both. Such complex systems are subject to failure due to the failure of any system component. Further, such complex systems, especially those including robotics, are expensive to manufacture and maintain.

SUMMARY OF THE INVENTION

Thus, a need has arisen for an efficient, simple to operate, and relatively low cost apparatus for performing a high throughput of chemical assays and biological reactions at reaction sites on a substrate.

A further need has arisen for apparatus which allows high-throughput analyzing and screening techniques for chemical assays of biochemical reactions within an aliquot or between aliquots to be performed at discrete reaction sites. Further, it is a feature of the invention that the delivery of aliquot(s) may be accurately and automatically controlled and monitored, e.g., by a rotatable substrate and a movable fluid dispenser. It is a technical advantage of the invention that etch geometry may be used to form reaction sites which may have added advantages in that they may reduce evaporation and aid in the retention of a portion of the fluid.

Yet a further need has arisen for easily assembled and simply and accurately controlled apparatus for delivering an aliquot or aliquots to reaction sites in order to perform chemical or biochemical testing, or both. It is a feature of the invention that the apparatus achieves a high degree of accuracy in the delivery of fluids to reaction sites. It is a technical advantage of the apparatus that it may employ prepackaged engines or motors, such as linear and rotary stepper motors, to move and position at least one fluid dispenser outlet over a reaction site. Such stepper motors provide a high degree of accuracy and repeatability of movement. Such stepper motors also permit the use of an integrated control system with electronic damping and an integrated indexing system. Moreover, the control systems for such stepper motors may readily be customized to provide for variable speed and continuous speed operation.

Still a further need has arisen for an apparatus which aligns at least one fluid dispenser outlet with at least on reaction site without the use of complex robotics. It is a technical advantage that the linear stepper motor(s) move(s) the fluid dispenser outlet(s) in one dimension along at least one rail, and that the rotary stepper motor(s) rotate(s) the substrate around an axis. It is a further technical advantage of the use of linear and rotary stepper motors that they may be less expensive to manufacture, maintain, and replace than complex robotics.

Yet another need has arisen for an apparatus having a multi-function head comprising at least one fluid dispenser for delivering a fluid or fluids to one and at least one of a plurality of reaction sites and at least one readout device.

The readout device(s) may serve a plurality of functions including monitoring the progress of assays, scanning the reaction site(s) to determine the results of assays, locating a reaction site or sites by reading a locating mark, and guiding at least one dispenser outlet to a reaction site or sites by means of a tracking mark. It is a technical advantage of the multi-function head that the operation and construction of the apparatus is simplified by the combination of multiple functions on a single movable head. It is a further technical advantage of the multi-function head that a single control system may position both the at least one fluid dispenser and the at least one readout device, thereby eliminating alignment differences between these components. It is yet another technical advantage of the multi-function head that rapidly or instantaneously occurring assays may be monitored immediately after initiation and monitored until completion. It is still another technical advantage of the apparatus that a micropositioner, such as a three-axis micropositioner, may be controlled to make adjustments, e.g., adjustment is a range of less than about 15 mm with an accuracy of about one micron, along Cartesian axes in the position of the at least one fluid dispenser outlet and the readout device.

The invention is an apparatus for performing a plurality of assays, such as a plurality of chemical assays or a plurality of biochemical reactions comprising an axially rotatable substrate including a plurality of radially-arrayed reaction sites. Other assays include cellular assays as well as physical and biophysical assays, e.g., chemiluminescence luminescence, dielectric field strength, resistivity, impedance, circular dichroism, refractivity, surface plasmon resonance, optical absorbance, magnetic resonance, and the like. Assay components may include, for example, synthetic organic compounds (e.g., compounds of less than 100,000 molecular weight, preferably compounds of less than 10,000 molecular weight, more preferably compounds of less than 1,000 molecular weight) proteins (e.g., enzymes, amyloid proteins, receptors, cytokines, and antibodies) peptides, oligopeptides, nucleic acids (including modified synthetic derivatives thereof, DNA, RNA oligonucleotide and monomeric nucleotides, nucleosides, modified synthetic variants thereof, and the like) cells (e.g., bacterial cells; yeast or other fungal cells; unicellular organisms such as protozoans; animal cells including insect, avian, and mammalian cells; and plant cells) cell membranes and other cellular components, buffers, salts, ions such as metal ions, lipids, carbohydrates, vitamins, extracellular matrixes or components thereof, as well as blood serum, or other bodily fluids.

The substrate may be manufactured from glass, ceramics, semiconductor materials, plastics, composites, and combinations thereof. Semiconductor materials are solid crystalline materials whose electrical conductivity is intermediate between that of a conductor and an insulator, ranging from $10^5$ mhos and $10^{-7}$ mho per meter and is usually strongly temperature dependant. Semiconductor materials may include silicon, germanium, and gray tin. For example, the substrate may include a plurality of layers of semiconductor material which may partially or completely cover the surface of the substrate. Alternatively, the plurality of layers may lie beneath the surface of the substrate and extend for a portion or for the entire area of the substrate.

The apparatus further comprises means for rotating and controlling the rotation of the substrate and at least one fluid dispenser for conveying at least one fluid to at least one of the reaction sites. The means for rotating may comprise a engine, such as an air driven turbine, or a motor. Each of such fluid dispensers includes a fluid dispenser outlet. In addition, the apparatus includes means for identifying the at least one reaction site, and means for aligning the at least one fluid dispenser outlet with the at least one reaction site.

In particular, the apparatus may comprise at least one multi-function head, such as a dual function head, including at least one fluid dispenser for conveying at least one fluid to at least one of the reaction sites and at least one readout device. The readout device may include means for locating a reaction site, such as the means for identifying a location mark, and for monitoring the chemical or biochemical reactions at the reaction sites. Each of such fluid dispensers includes a fluid dispenser outlet. Thus, the fluidics and locating and monitoring functions of the apparatus may be combined in a multi-function head.

The operation of stepper motors is known in the art. For example, such motors are used in computer disk drives. Generally, a stepper motor rotates in short, essentially uniform regular movements. The stepped movements are obtained by means of electromagnetic controls. Although the apparatus may include a rotary stepper motor, the means for rotating also may rotate the substrate at an adjustable or substantially continuous speed, or both, and may control the rotation of the substrate by adjusting the speed and a direction of rotation. Further, the means for rotating is controllable to rotate the substrate at a speed, such that a portion of the at least one fluid is removable from the at least one reaction site by a centrifugal force generated by the rotation of the substrate. Moreover, at least one channel may join the at least one reaction site to at least one other reaction site. The means for rotating further may be controllable to rotate the substrate at a speed, such that the at least one fluid is drawn from the at least one reaction site through the at least one channel to the at least one other reaction site by a centrifugal force generated by the rotation of the substrate.

The fluid(s) delivered to the reaction site may comprise at least a first amount of at least one fluid aliquot and at least a second amount of at least one separating fluid, e.g., a solvent, oil, air, immiscible fluid, or the like. For example, the first amount of at least one fluid aliquot may be substantially identical to the second amount of at least on separating fluid. In another embodiment, however, the first amounts of the at least one fluid aliquot may be substantially identical to each other while the second amounts of the at least one separately fluid are of a different amount and are substantially identical to each other. For example, an oil or air may be a preferred separating fluid for water-based aliquots. Further, the at least one fluid dispenser may include one or more pumps, suction devices, and timing devices for controlling the pump(s) or the suction device(s), or both. The pump(s) may include conduits and valves, whereby the pump(s) may alternately draw at least one of the first amount, e.g., in a range of about 0.0001 to 5 $\mu$l, and preferable about 3 to 5 $\mu$l, of the at least one fluid aliquot and at least one of the second amount of the at least one separating fluid into the dispenser tube and delivers an alternating stream of the at least one aliquot and the at least one separating fluid to the at least one fluid dispenser outlet under a controlled pressure differential relative to the ambient pressure surrounding the fluid dispenser outlet(s). The timing device(s) then may control the operation of the suction device(s), such that the suction device(s) may draw off the stream from the fluid dispenser outlet(s).

Specifically, the timing device(s) may measure a flow rate of the stream through the dispenser tube and deactivate and subsequently reactivate the suction device(s), such that at least one first amount of the at least one aliquot is delivered to the reaction site. The suction device(s) may create a suction pressure less than the ambient pressure surrounding the dispenser outlet(s), e.g., a vacuum sufficient to remove fluid from the dispenser outlet(s). Alternatively, a plurality of suction devices may create different degrees of pressure differential across the orifices of such suction devices, e g., different levels of vacuum, with respect to the ambient pressure surrounding the dispenser outlet(s). In still another alternative, a library of tubes may be provided, each tube having a predetermined amount of a chemical or solution for use in performing a chemical assay or causing biological reaction. A desired amount of the chemical solution may then be drawn or pumped from the tube and deposited at a reaction site or reaction sites. The unused portion of the chemical or solution may be discarded or recovered for recycling or reuse, or the tube also may be discarded or refilled, sealed, and reused. Other means for dispensing or removing fluids at reaction sites also may be used in accordance with the invention. See, e.g., D. W. Brandt, *Multiplexed Nanoliter Transfers for High Throughput Drug Screening Using the BIOMEK* 2000 *and the High Density Replicating Tool*, J. BIOMOLECULAR SCREENING 2:111–116 (1997); which is incorporated herein by reference to more fully describe the state of the art to which the present invention pertains.

The dispenser outlet(s) may be movably mounted on a rail which transects the substrate and is oriented substantially parallel to a surface of the substrate, e.g., is suspended over the substrate, and a first motor may be used to rotate the substrate. The means for aligning comprises a second motor for positioning the at least one fluid dispenser outlet along the rail. Moreover, as noted above, the first motor may be a rotary stepper motor, and the second motor may be a linear stepper motor. In addition, the means for aligning may comprise a computer (including a microprocessor or other electronic device) which receives, processes, and presents data, and which stores a start location on the substrate's surface for the dispenser outlet. The computer and additional, functionally linked electronics including, for example, a signal generator such as an electromagnetic energy source, and a calibrating sensor, such as an electromagnetic energy sensor, may provide movement signals to the first and second motor. Thus, the computer and the additional electronics generate signals to align the dispenser outlet over the reaction site. Alternatively, the fluid dispenser outlet(s) may be mounted on a pivotable arm which may be rotated through an arc across the surface of, e.g., over, the rotating substrate. In this embodiment, the second motor may also be a rotary stepper motor.

In addition, the apparatus may position the multi-function head by means of a two step process. First, the apparatus may direct the head to the general vicinity of a selected reaction site. Second, the multi-function head may utilize the means for identifying to interrogate or read the locating marks to identify the selected reaction site and to align the dispenser with that reaction site.

The means for identifying may include at least one sensor. This sensor may be positioned in the same manner as the fluid dispenser outlet, e.g., it may be joined to a linear stepper motor which is mounted on a rail above the substrate. Preferably, the sensor is incorporated into the head. This at least one sensor may receive a signal emanating from the substrate, or the at least one sensor may transmit an interrogating signal and receive a locating signal in response. Further, the at least one sensor may read at least one locating mark, e.g., an indexing mark, a tracking mark, a bar code, or combinations thereof, on the substrate's surface. Examples of the locating mark are discussed below. See FIG. 7. However, as noted above the locating mark may consist of an indexing mark, which identifies the particular reaction site, and at least one tracking mark which helps the means for aligning to guide the multi-function head and its associated fluid dispenser(s) and readout device(s) over the reaction site. In particular, the tracking mark may be recognized and help guide the head to the reaction site by its size or shape or by its physical relationship to, i.e., distance from or direction to the reaction site.

In another embodiment of the invention, the apparatus for performing a plurality of assays again comprises an axially rotatable substrate including a plurality of radially, arrayed reaction sites; means for rotating the substrate; and at least one multi-function head including at least one fluid dispenser for conveying at least one fluid to at least one of the reaction sites and at least one readout device. The at least one fluid dispenser also may include at least one fluid dispenser outlet. The apparatus also may include means for identifying the at least one reaction site and means for aligning the at least one multi-function head, such that the at least one fluid dispenser outlet is aligned with the at least one reaction site. The means for rotating may be controllable to rotate the substrate at a speed, such that a portion of the at least one fluid is removable from the at least one reaction site by a centrifugal force generated by the rotation of the substrate.

In still another embodiment of the invention, the apparatus for performing a plurality of assays comprises an axially rotatable substrate including a plurality of radially-arrayed reaction sites; means for rotating the substrate; at least one fluid dispenser for conveying at least one fluid to at least one dispersion point, preferably located on the substrate; and means for identifying at least one of the reaction sites. Further, the apparatus, and preferably the substrate, may include at least one channel joining the at least one dispersion point to the at least one reaction site. Alternatively, this embodiment may include at least one multi-function head including at least one fluid dispenser for conveying at least one fluid to at least one dispersion point and at least one readout device. The means for rotating may be controllable to rotate said substrate at a speed, such that the at least one fluid is conveyed from the at least one dispersion point to the at least one reaction site by a centrifugal force generated by the rotation of the substrate.

In yet another embodiment of the invention, the apparatus for performing a plurality of assays comprises an axially rotatable substrate including a plurality of radially-arrayed reaction sites; at least one fluid dispenser for conveying at least one fluid to the substrate; means for identifying at least one of the reaction sites; and means for rotating the substrate. For example, the at least one fluid dispenser may convey at least one fluid to the substrate through a spindle around which the substrate rotates. The means for rotating is controllable to rotate the substrate at a speed, such that the at least one fluid is drawn across the reaction sites by a centrifugal force generated by the rotation of the substrate.

Other features and technical advantages will be apparent to persons skilled in the relevant art in view of the following detailed description and accompanying drawings.

BRIEF DESCRIPTION OF THE DRAWINGS

For a more complete understanding of the present invention and the technical advantages thereof, reference now is made to the following description taken in conjunction with the accompanying drawings, in which like reference numerals represent like referenced parts, wherein:

FIGS. 2B and 2C depict two embodiments of a delivery mechanism for controlling the delivery of fluids through the fluid dispenser outlet to the reaction sites;

FIG. 4C is an enlarged view of an aliquot in a fluid inlet tube 20';

DETAILED DESCRIPTION OF PREFERRED EMBODIMENTS

Figure 1:
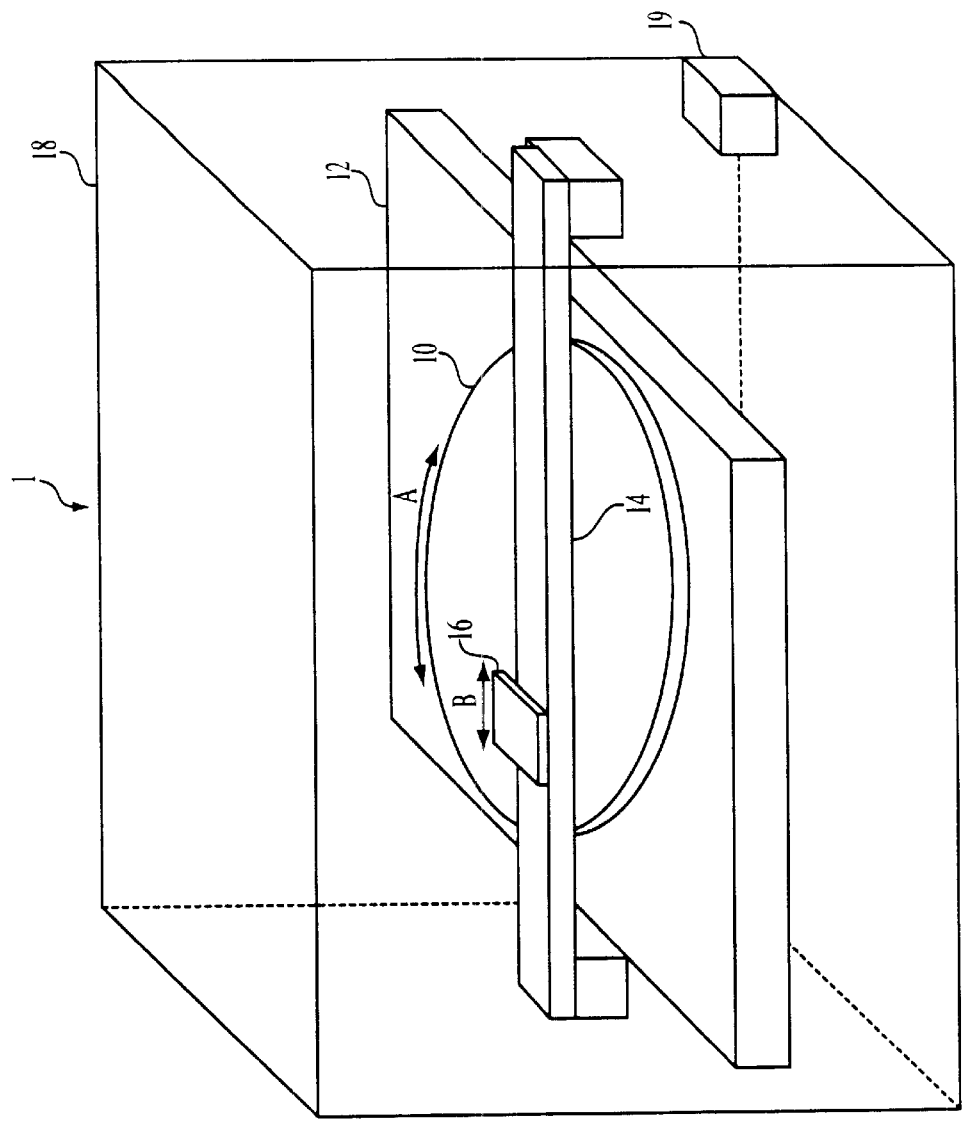
FIG. 1 depicts a perspective view of a first embodiment of the apparatus of the present invention.

Referring to FIG. 1, a perspective view of a first embodiment of the apparatus of the present invention is depicted. An apparatus 1 for delivering fluid to a reaction site includes a substrate 10, such as a silicon wafer, mounted on a platform 12, which includes a rotary stepper motor (not shown), such as a Zeta 57-51-10 Motor and a Zeta 4 Rotary Driver manufactured by Parker Compumotor Company of Rohnert Park, Calif., U.S.A. The rotary stepper motor rotates substrate 10 in the directions of arrow A. A rail 14 is suspended above and transects, e.g., bisects, substrate 10. A linear stepper motor 16, such as a L20 Stepper Motor, manufactured by Parker Compumotor Company of Rohnert Park, Calif., U.S.A., is mounted on rail 14, such that linear stepper motor 16 is movable in one dimension in the directions of arrow B along rail 14 over the surface of substrate 10.

The rotary stepper motor is controllable to rotate substrate 10 at a plurality of variable and continuous speeds in either direction of arrow A. For example, an AT6200 Controller, manufactured by Parker Compumotor Company of Rohnert Park, Calif., U.S.A., may be used to control the operation of the rotary stepper motor. Further, the rotary stepper motor may be operated to rotate substrate 10 continuously in a manner similar to that of the disk in a compact disc player, so that a centrifugal force is generated on substrate 10, or incrementally, so that substrate 10 may be moved a less than one revolution with respect to the position of linear stepper motor 16.

Substrate 10, platform 12, rail 14, and linear stepper motor 16 may be enclosed within a container 18. Container 18 allows the atmosphere surrounding the reaction sites to be strictly monitored and controlled during testing. Container 18 may be airtight to prevent dust and moisture from settling on and effecting the operation of linear stepper motor 16 or the rotary stepper motor and to permit the maintenance of positive or negative pressure within container 18. Moreover, dust and moisture may adversely effect the chemical or biochemical reactions, or both, occurring at the reaction sites and alter the outcomes of chemical and biochemical tests. For example, container 18 may be equipped with a humidity and temperature sensor 19, so that the level of and changes in humidity and temperature may be detected. When low or high relative humidity or temperature, or both, is (are) detected, assaying operations may be terminated, or the atmospheric conditions within container 18 may be corrected. Changes in humidity or temperature, or both, may cause evaporation of all or a portion of the deposited fluid or dilution of the fluid with condensation. In addition, the container environment may be controlled by establishing a vacuum, increasing air pressure, regulating environmental temperature, or establishing a predetermined container atmosphere, such as a nitrogen atmosphere, an oxygen-rich atmosphere, a nobel gas (inert) atmosphere, or a combination thereof. Further, because of the importance of delivering precise amounts of fluid to small reaction sites, container 18 also serves to reduce or eliminate air disturbances at or near the surface of substrate 10.

Figure 2A:
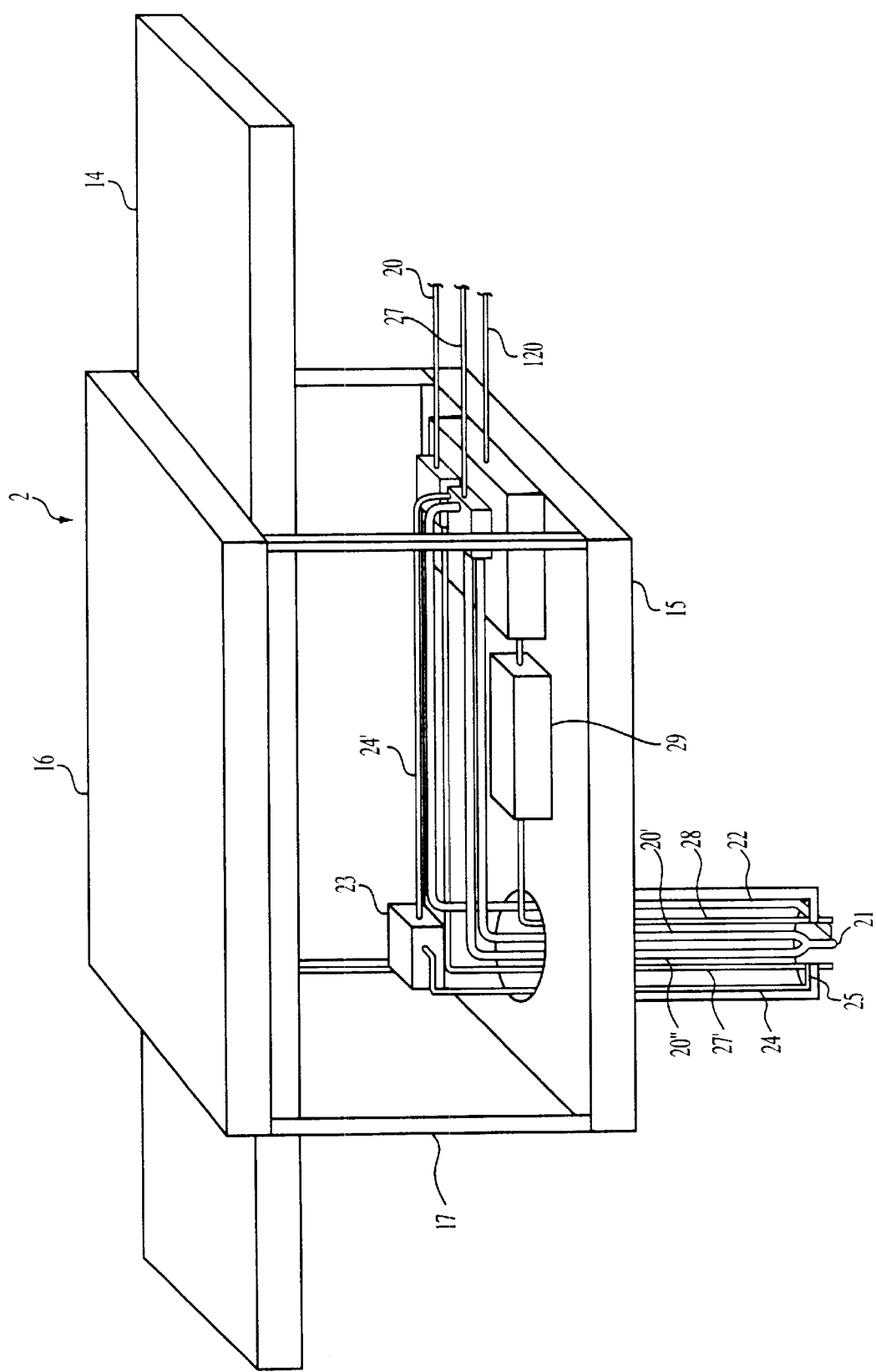
FIG. 2A depicts a perspective view of a fluid dispenser with a fluid dispenser outlet mounted on a linear stepper motor.

FIG. 2A depicts a perspective view of a fluid dispenser 2, which may include linear stepper motor 16 and which may be mounted on rail 14. Referring to FIG. 2A, a fluid stream comprising a serialization of measured amounts of aliquot(s) and measured amounts of separating fluid(s) is delivered to fluid dispenser 2 through a fluid input/return tube 20. Fluid dispenser 2 includes a dispenser platform 15 that is suspended below linear stepper motor 16 by four dispenser platform supports 17. Components relating to the aligning of a dispenser outlet 21 over a reaction site on substrate 10 also may be mounted and stabilized on platform 15. Preferably, the length of fluid dispenser outlet 21 is minimized in order to reduce or eliminate dead space.

From fluid input/return tube 20, the fluid is received by a fluid input tube 20' and delivered to fluid dispenser outlet 21. Fluid, which is not delivered to dispenser outlet 21, is returned to fluid input/return tube 20 through a fluid return tube 20". Further, fluid that is delivered to dispenser outlet 21, but which is not delivered to substrate 10 may be withdrawn through suction return tube 22. A suction device (not shown) draws undelivered fluid from dispenser outlet 21. The suction device creates a pressure differential across the orifice of suction return tube 22, such that the pressure in suction return tube 22 is less than the ambient pressure surrounding the dispenser outlet(s), e.g., a vacuum sufficient to remove fluid exiting dispenser outlet 21.

Linear stepper motor 16 receives movement signals from an external computer (not shown) through a computer connection (not shown). Similarly, a timing device 23, e.g., an electronic timing device, may measure flow rate and determine the amount of fluid delivered from dispenser outlet 21 by means of at least one flow sensor 25 positioned adjacent to dispenser outlet 21. For example, flow sensors 25 may detect the interruption or diminution of an electromagnetic energy beam, e.g., a laser or high intensity light beam, directed across the orifice of dispenser outlet 21. Flow sensors 25 may be connected to timing device 23 by a timing connection line 24. Further, timing device 23 may send signals over a timing signal return line 24' and a signal transfer line 120 to a computer (not shown) to activate and deactivate the suction device (not shown), and thereby control the amount of fluid delivered to substrate 10 through dispenser outlet 21.

In addition, a fluid dispenser 2 may include a detection mechanism, e.g., these components may comprise a multi-function head, to determine whether and to what extent a chemical reaction has occurred at a reaction site. A light source (not shown) may supply high intensity light to fluid dispenser 2 through a light source input 27 to a light input optical fiber 27'. Light input optical fiber 27' is fixed adjacent to dispenser outlet 21, so that high intensity light may be directed onto at least one reaction site of substrate 10. The amount and nature of the light reflected from the reaction site may indicate the occurrence and progress of the reaction. Such reflected light may be collected by a light receiving optical fiber 28, a receiving end of which also may be positioned adjacent to dispenser outlet 21. Further, light from light input optical fiber 27' may stimulate fluorescence at the at least one reaction site, and such fluorescence may by detected by light receiving optical fiber 28. Light received by light receiving optical fiber 28 is conducted to a photomultiplier tube 29 that includes a band pass filter and generates an electrical signal describing the nature and amount of the light reflected from the at least one reaction site. Such a photomultiplier tube may also be a photo-diode array. Photo-diode arrays are known light detecting elements of a charge coupled device (CCD). Alternatively, a source of electromagnetic energy may be supplied to detection mechanism and directed onto at least one reaction site of substrate 10. Again, the amount and nature of the reflected electromagnetic energy may indicate the occurrence and progress of the reaction. This signal then is returned to a computer (not shown) for analysis over signal transfer line 120.

Additionally, at least one sensor may be mounted on fluid dispenser 2 in order to identify reaction sites or to aid in determining a start location for dispenser outlet 21 with respect to the surface of substrate 10, or both. In particular, the at least one sensor may receive a signal emanating from an emitter positioned on substrate 10 (see FIG. 9C, described below), or the at least one sensor may transmit an interrogating signal to substrate 10, e.g., to a transponder positioned adjacent to a reaction site or group of reaction sites, and then receive a locating signal in response. Further, the at least one sensor may read, i.e., scan, at least one locating mark, e.g., an indexing mark or a bar code, on the surface of substrate 10. Such a locating mark also may include a tracking mark to guide Fluid dispenser 2 to a reaction site. Bar codes, micro-scale bar codes, and bar code readers are known in the art.

FIGS. 2B and 2C depict two embodiments of a delivery mechanism 200 and 200', respectively, for controlling the delivery of fluids through a dispenser outlet to the reaction sites. Referring to FIG. 2B, delivery mechanism 200 includes a portion of fluid input tube 20' and a portion of fluid return tube 20" forming a U-shaped connection. Arrows F depict the flow path of the serialized fluid through the U-shaped connection. Dispenser outlet 21 extends substantially perpendicular to the fluid flow path as fluid passes from fluid input tube 20' into fluid return tube 20". A first electro-mechanical controller 202, such as a solenoid, controls a return side valve 204, and first controller 202 may receive control signals 206 from timing device 23. Preferably, first controller 202 and return side valve 204 are positioned sufficiently distant from dispenser outlet 21, such that vibrations or movement, or both, caused by the operation of first controller 202 or return side valve 204, or both, do not effect the alignment of dispenser outlet 21 over at least one reaction site on substrate 10.

Fluid may be supplied to fluid input tube 20' under a pressure differential determined relative to the ambient air pressure within container 18. Nevertheless, this pressure is sufficient to force the majority of the fluid in fluid input tube 20' to pass directly across dispenser outlet orifice 208 and into fluid return tube 20", and any fluid entering dispenser outlet 21 may been collected by the suction device (not shown) through suction return tube 22. However, when return side valve 204 is closed, fluid from fluid input tube 20' flows directly into dispenser outlet 21. Moreover, because dispenser outlet 21 may narrow toward a dispenser outlet tip 210, the flow velocity of fluid leaving dispenser outlet 21 may be greater than the flow velocity within fluid input tube 20'.

For example, dispenser outlet orifice 210 may have a diameter of less than about 10 μm and preferably, less than about 4 μm. At a flow rate of about 2 μl/sec., a pressure differential in a range of about 0.01 to 2000 psi is created across dispenser outlet orifice 210, and preferably, a positive pressure in a range of about 50 to 500 psi. If a suction device is used to draw off portions of the flow of serialized fluid from dispenser outlet orifice 210, a similar, but inverse, pressure differential is created across the orifice of suction return tube 22 adjacent to dispenser outlet orifice 210.

Referring to FIG. 2C, delivery mechanism 200' also includes a portion of fluid input tube 20' and a portion of fluid return tube 20" forming a U-shaped connection. Arrows F again depict the flow path of the serialized fluid through the U-shaped connection. Dispenser outlet 21 extends substantially perpendicular to the fluid flow path as fluid passes from fluid input tube 20' into fluid return tube 20". First controller 202 controls return side valve 204, and first solenoid 206 again may receive control signals 206 from timing device 23. Further, a second electro-mechanical controller 212, such as a solenoid, controls an input side valve 214, and second controller 212 also may receive control signals 206 from timing device 23. In addition, delivery mechanism 200' includes a four-way connection 216 having dispenser outlet orifice 208 providing access to dispenser outlet 21 and a dispenser fluid pump orifice 218 providing access to dispenser fluids (not shown) provided by a dispenser fluid pump 220. The dispenser fluids may be the same as the separating fluid(s) in the serialized fluid. Preferably, first and second controllers 202 and 212, return side valve 204, input side valve 214, dispenser fluid pump 220 are positioned sufficiently distant from dispenser outlet 21, such that vibrations or movement, or both, caused by the operation of any or all of these components does (do) not effect the alignment of dispenser outlet 21 over at least one reaction site on substrate 10.

As noted above, fluid may be supplied to fluid input tube 20' under a small pressure differential, e.g., less than about 10 psi, and preferably less than about 2.5 psi, determined relative to the ambient pressure within container 18. Nevertheless, this pressure is sufficient to force the majority of the fluid in fluid input tube 20' to pass directly across dispenser outlet connection 208 and dispenser fluid pump connection 218 and into fluid return tube 20". However, when return side valve 204 and input side valve 214 are closed and a dispenser fluid, such as a separating fluid is pumped into dispenser fluid pump orifice 218 by dispenser fluid pump 220, fluid from fluid input tube 20' flows directly into dispenser outlet 21. Moreover, because dispenser outlet 21 may narrow toward dispenser outlet orifice 210, the flow velocity of fluid leaving dispenser outlet 21 may be greater than the flow velocity within fluid input tube 20'.

Essentially, delivery mechanisms 200 and 200' redirect the flow of fluid in fluid input tube 20' into dispenser outlet 21. In delivery mechanism 200, control of the amount of fluid and the number and type of aliquot(s) supplied to the various reaction sites on substrate 10 may be accomplished by the control of return side valve 204. Similarly, in delivery mechanism 200', control of the amount of fluid and the number and type of aliquot(s) supplied to the various reaction sites on substrate 10 may be accomplished by the control of return side valve 204 and input side valve 214, as well as dispenser fluid pump 220. Alternatively, or in addition to the fluid dispensing control accomplished by controlling valves 204 and 214 and pump 220, the suction device (not shown) may be used to draw off fluid through suction return tube 22 and thereby, controlling the amount of fluid dispensed from dispenser outlet 21 that is delivered to substrate 10.

Delivery mechanisms 200 and 200' may comprise of channels and micro-mechanical devices formed within a block of material, such as a plurality of layers of semiconductor material. For example, grooves or trenches may be etched into a block of semiconductor material and micromechanical devices, such as valves 204 and 214, may be formed integrally with the grooves or trenches. A second block of semiconductor material may be joined to the etched block to cover the grooves or trenches to form tube-like channels.

Alternatively, the fluid dispenser may employ ink-jet technology to provide measured amounts of aliquot(s) to reaction sites on the substrate surface. In another embodiment, a fluid dispenser may eject a micro-droplet stream of the at least one fluid from the dispenser outlet, and an electrostatic accelerator and deflector may direct the micro-droplet stream to at least one of the reaction sites. Moreover, a fluid dispenser may include a micro-fluidic device employing an oscillating solenoid for pumping fluid from a capillary tube or a piezoelectric device having a piezoelectric tube to dispense measured aliquots separated by air from a capillary tube, or the like. Because the aliquots are separated by air, excessive dilution of the aliquots is avoided.

Such devices also may include the BioJet Quanti3000™ fluid dispenser, which is manufactured by BioDot, Inc. of Irvin, Calif., U.S.A. This device employs an inkdot-type fluid delivery system. This device may achieve flow rates up to 50 μl/sec. of a fluid having a viscosity in a range of 1 to 20 centipoise. This range of flow rates, however, may be extended dependent on fluid rheology. Moreover, this device may deliver lines of fluid with volumes as low as 250 nl/cm and line widths in a range of 0.25 to 5 mm. The specifications were determined by dispensing deionized water with 0.5% surfactant added. This device also may deliver droplets of fluid with volumes as low as 4 nl/droplet and droplet diameters in a range of 0.25 to 5 mm. Achievable droplet volumes and diameters are dependent upon fluid and fluid membrane characteristics. BioJet Quanti3000™ fluid dispenser may achieve a flow repeatability of less than 1% cumulative volume variations for delivered lines and of less than 5% variation between drops.

The BioJet Quanti3000™ fluid dispenser carries a swept volume of less than 40 μl and is supplied by a feeding tube carrying 5 μl/cm. In addition, this fluid dispenser may be equipped with a filter the fluid reagents before delivery to a reaction site. Such a filter may provide for removal of particulates with a diameter of less than 10 microns. Moreover, the fluid dispenser may be equipped with means for de-aerating the fluid flow. These devices may employ an oscillating solenoid, for example, a solenoid oscillating at a rate of about 100 Hz, for pumping fluid from a capillary tube or a piezoelectric tube that is excited by frequencies up to about 1000 Hz which surrounds a capillary tube, respectively. Such devices may achieve flow rates of less than about 10 to 500 μl/sec., and preferably, of less than about 200 μl/sec., the orifices of the capillary tubes of these devices may have a diameter in a range of about 50 to 175 μm.

Figure 3:
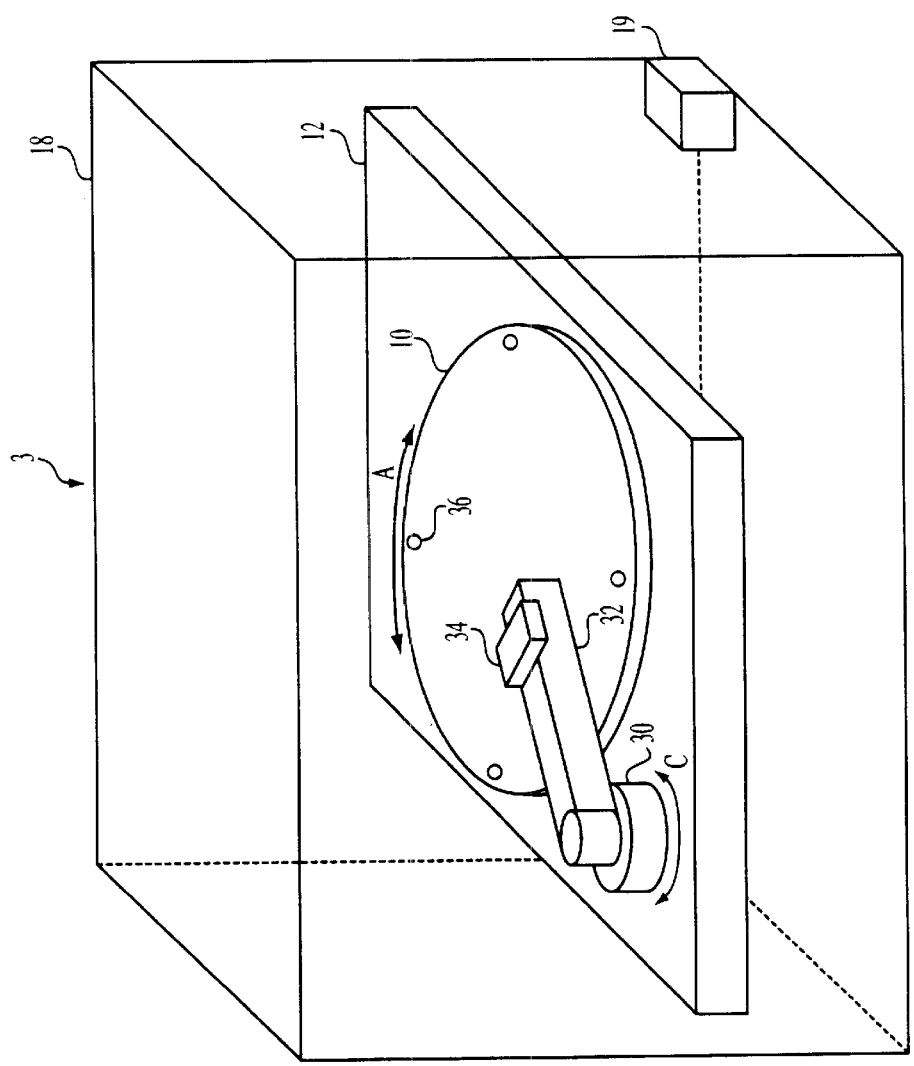
FIG. 3 depicts a perspective view of a second embodiment of the apparatus of the present invention including a fluid dispenser mounted on a pivotable arm and a calibrating device.

FIG. 3 depicts a perspective view of a second embodiment of the apparatus of the present invention. An apparatus 3 for delivering fluid to a reaction site includes substrate 10, such as a silicon wafer, mounted on platform 12, which includes a first rotary stepper motor (not shown), such as a Zeta 57-51-10 Motor and a Zeta 4 Rotary Driver. The first rotary stepper motor rotates substrate 10 in the directions of arrow A. A second rotary stepper motor 30, such as a Zeta 57-51-10 Motor or a Zeta 4 Rotary Driver, is mounted on platform 12, and a pivot arm 32 is mounted on second rotary stepper motor 30. A fluid dispenser 34 is mounted on pivot arm 32, and pivot arm 32 is of sufficiently length, such that fluid dispenser 34 may be rotated through an arc in two dimensions by the rotation of second rotary stepper motor 30 in the directions of arrow C to reach the entire surface of rotating substrate 10.

The first rotary stepper motor is controllable to rotate substrate 10 at a variety of speeds in either direction of arrow A. For example, an AT6200 Controller may be used to control the operation of the first rotary stepper motor. Further, the first rotary stepper motor may be operated continuously, so that a centrifugal force is generated on substrate 10, or incrementally, so that substrate 10 may be moved less than one revolution and stopped at a new orientation with respect to the position of fluid dispenser 34. For example, pivot arm 32 may be operated in a manner similar to that of a tracking arm of a hard disk magnetic computer memory. A first rotary stepper motor may rotate substrate 10, while fluid dispenser 34 is positioned over substrate 10 by the rotary motion of rotating second rotary stepper motor 30 to pivot arm 32.

Substrate 10, platform 12, second stepper motor 30, pivot arm 32, and fluid dispenser 34 may be enclosed within container 18. Container 18 allows the atmosphere surrounding the reaction sites to be strictly monitored and controlled during testing. Container 18 may be airtight to prevent dust and moisture from settling on and effecting the operation of the rotary stepper motors and to permit the maintenance of positive or negative pressure within container 18. Moreover, dust and moisture may adversely effect the chemical and biochemical reactions occurring at the reaction sites and alter the outcomes of chemical and biochemical tests. For example, container 18 may be equipped with a humidity and temperature sensor 19, so that levels of and changes in humidity and temperature may detected. When low or high relative humidity or temperature, or both, is (are) detected, assaying operations may be terminated or the atmospheric conditions within container 18 may be corrected. Further, because of the importance of delivering precise amounts of fluid to small reaction sites, container 18 also serves to reduce or eliminate air disturbances at or near the surface of substrate 10.

In addition, substrate 10 may be equipped with a plurality of calibrating holes 36. Such calibrating holes 36 may be employed in combination with or in place of the locating marks described above. For example, substrate 10 may include four calibrating holes 36 positioned around the outer circumference of substrate 10 at 90° intervals. An electromagnetic energy sensor (not shown) may be aligned beneath each of calibrating holes 36, such that when an electromagnetic energy source (not shown), which may be mounted on fluid dispenser 34, is directly over one of calibrating holes 36 electromagnetic energy generated by the electromagnetic energy source is detected by the corresponding electromagnetic energy sensor. This combination of the electromagnetic energy source with corresponding electromagnetic energy sensors may be used to locate fluid dispenser 34 over substrate 10 and to calibrate the aligning means of fluid dispenser 34. Further, each reaction site may be positioned a precise number of stepper motor "steps" from each other and from at least one of calibrating holes 36. Therefore, once fluid dispenser 34 locates and identifies one of calibrating holes 36, fluid dispenser 34 may be moved quickly and precisely between reaction sites and over the surface of substrate 10.

Figure 4A:
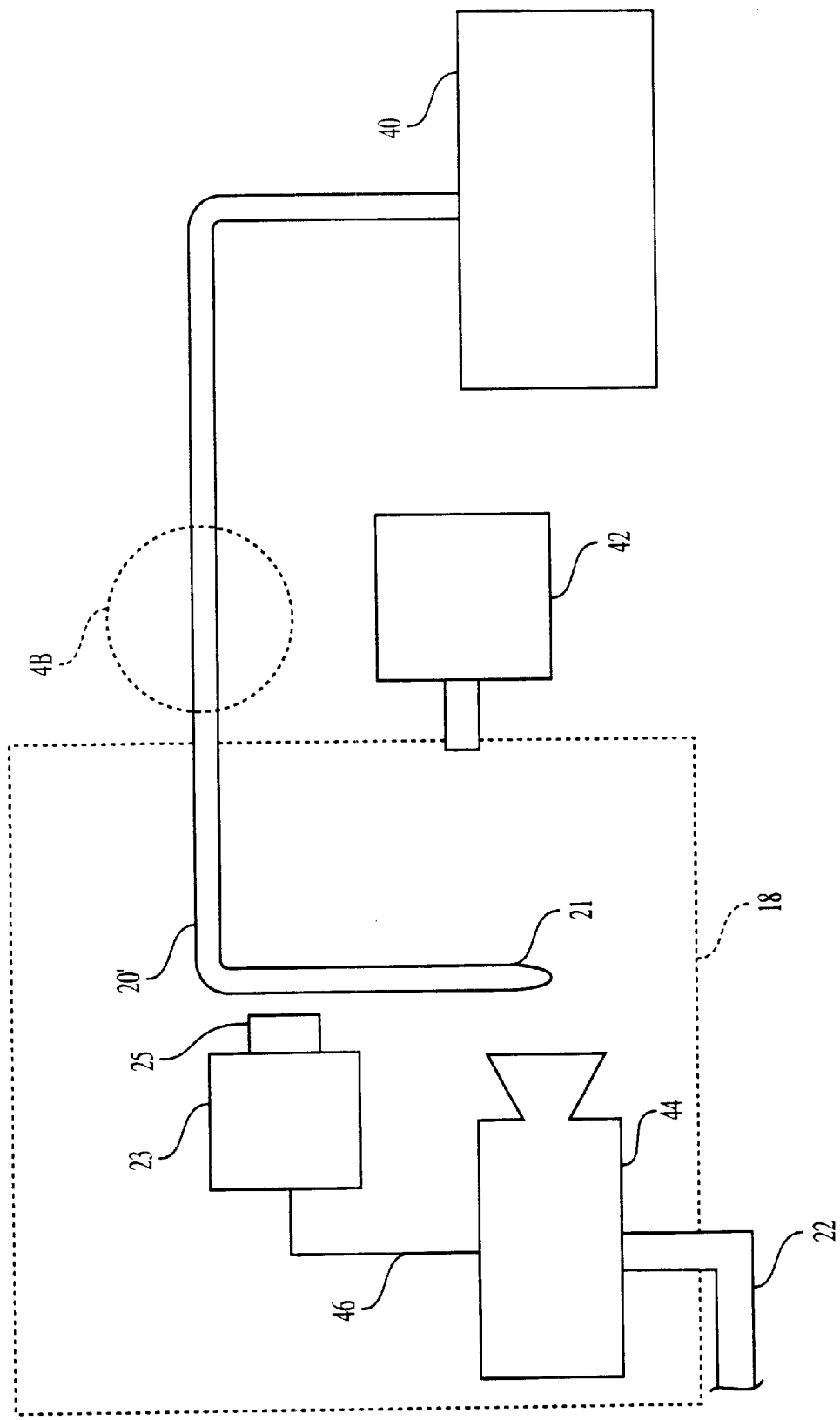
FIG. 4A is a schematic view of another embodiment of the fluid dispenser.

FIG. 4A is a schematic view of another embodiment of the fluid dispenser. A chemical or biological sample or samples are drawn from a fluid serializer 40, which accesses an aliquot fluid source and a separating fluid source (not shown). For example, in one embodiment of serializer 40, a pump may alternately draw amounts of an aliquot fluid or fluids from an aliquot fluid source through an aliquot fluid conduit and amounts of a separating fluid, such as a solvent, oil, air, immiscible fluid, a noble gas, or the like, from a separating fluid source through a separating fluid conduit, so that a serialized fluid stream, i.e., a fluid stream including alternating amounts of an aliquot or aliquots and amounts of separating fluid. Alternatively, serialized samples may be prepared as part of a serialized library, which are preformatted and stored for later use in the apparatus.

In another embodiment, a pressure control device 42, including an air pump and an air pressure gage, may create a vacuum within container 18, whereby amounts of aliquot fluid or fluids and amounts of separating fluid may be drawn into dispenser input tube 20'. For example, a valve may be used to alternatively place dispenser input tube 20' in communication with a source or sources of aliquot fluid or fluids and a source of a separating fluid. The vacuum in container 18 then may cause amounts of aliquot fluid or fluids and separating fluid to be drawn into dispenser input tube 20'. Alternatively, amounts of aliquot fluid or fluids and amounts of separating fluid may be formed as droplets, and an open end of dispenser input tube 20' may be positioned to draw selected droplets into dispenser input tube 20'.

Figure 4B:
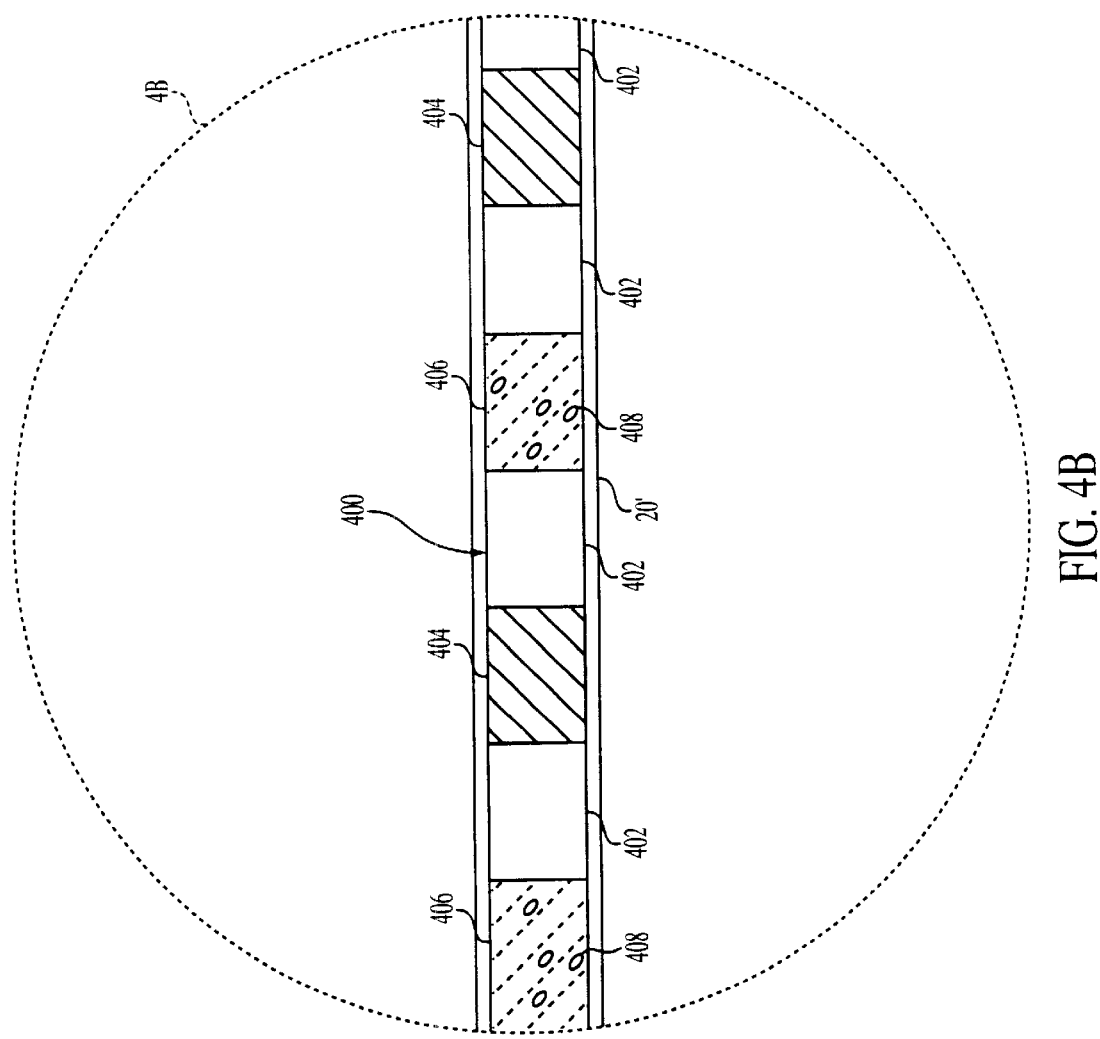
FIG. 4B is an enlarged view of a fluid inlet tube 20' illustrating a fluid including alternating amounts of aliquot and of a separating fluid.

FIG. 4B is an enlarged view of dispenser input tube 20' illustrating a serialized fluid stream including alternating amounts of one of two aliquot(s) and a separating fluid, such as an immiscible fluid or solvent. A solvent may be chosen as a separating fluid, so that aliquot residue is removed by the solvent as the serialized fluid passes through dispenser input tube 20'.

Referring again to FIG. 4A, a timing device 23 includes a flow sensor 25 to determine the rate of flow of the serialized fluid, so that activating and deactivating signals may be sent to suction device 44 via a timing signal connection 46. For example, the amounts of aliquot or separating fluid may include a component detectable by flow sensor 25. Fluid drawn from dispenser outlet 21 by suction device 44 is removed from the apparatus via suction return tube 22. As shown in FIG. 4A, the fluid dispenser outlet 21, as well as the fluid dispenser and the substrate, may be enclosed within container 18. Pressure control device 42 may be used to maintain a positive or negative pressure within container 18.

Referring to FIG. 4B, an enlarged view of a fluid inlet tube 20' is shown illustrating a fluid 400 including alternating amounts of aliquot and of a separating fluid. Specifically, fluid 400 comprises a separating fluid 402, a first fluid aliquot 404, and a second fluid aliquot 406. Second fluid aliquot 406 includes a plurality of flow sensor components 408. For example, components 408 may be magnetic beads, and such beads may be detected as they pass through fluid inlet tube 20' in close proximity to an coil or other magnetic sensor. If the diameter of fluid inlet tube 20', the order of serialization, and the amounts of aliquot and separating fluid are known, the flow rate of the serialized fluid stream may be determined. Further, the identity of each amount of aliquot or separating fluid may be determined from a signal generated by flow sensor components 408 in flow sensor 24, e.g., by varying the strength of the magnetic field generated by the magnetic beads or the density of the magnetic bead in an aliquot or a separating fluid, or both. Nevertheless, other types of sensor components may generate detectable signals such as fluorescence, radiation, electrical charge, or the like. For example, each fluid aliquot may have a volume in the range of about 3 to 5 μl, and preferably, in a range of about 4 to 5 μl. However, the amount delivered to any particular reaction site may be in a range of about 50 nanoliters (nl) to, and still more preferably, in a range of about 4 to 5 nl. In view of these volumes, timing device 23 may deactivate and reactivate suction device 44 or energize and de-energize first controller 202 or controllers 202 and 212 to deliver a measured amount of aliquot to a particular reaction site.

In order to control the amount of a fluid aliquot to be delivered to a reaction site, the frictional effects of contact between the aliquot and the inner surface of dispenser input tube 20' also are considered. Referring to FIG. 4C, a further enlargement of a portion of dispenser input tube 20' is shown. As first fluid aliquot 404 is pumped through dispenser input tube 20', friction between first aliquot 404 and the walls of dispenser input tube 20' causes the outer leading and trailing edges of the aliquot to mix with the separating fluid 402 and to create mixing zones 414. In order to ensure that pure aliquot portions are delivered to the reaction sites on substrate 10, delivered portions of first fluid aliquot 404 are drawn from within aliquot boundaries 416. A leading edge 410 and a trailing edge 412 of first fluid aliquot 404 are formed in the direction of fluid flow. Aliquot boundaries 416 identify the portion of the aliquot unaffected by frictional forces and by mixing with the separating fluid 402. The location of aliquot boundaries 416 depends in part on the pressure at which fluid 400 is pumped, the composition of first fluid aliquot 404, and the material of dispenser input tube 20'.

Figure 5:
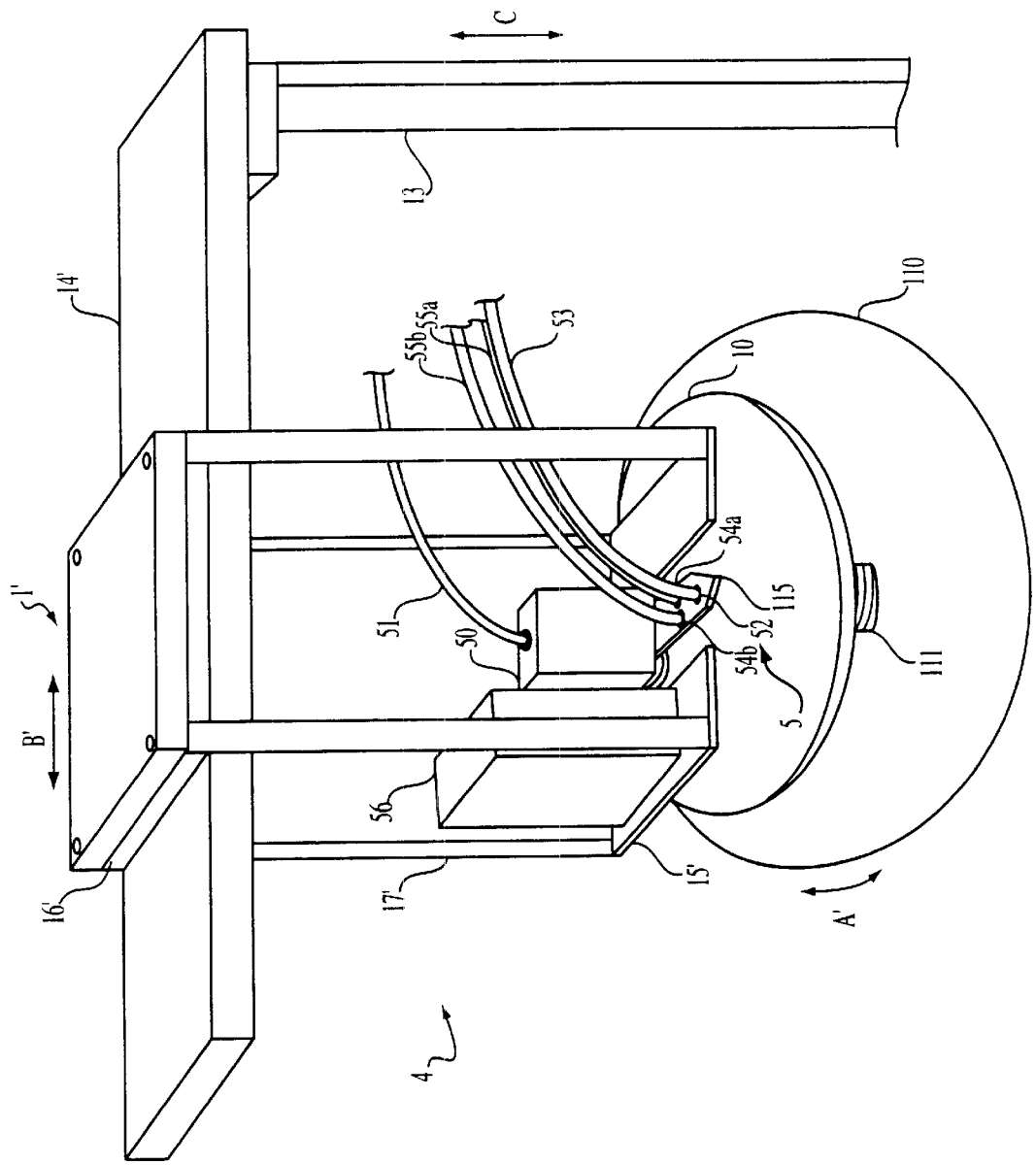
FIG. 5 depicts a perspective view of a third embodiment of the apparatus of the present invention including a multi-function head comprising a fluid dispenser and a readout device.

Referring to FIG. 5, a third embodiment of the apparatus 1' may include a multi-function head 4 including at least one fluid dispenser 50 for conveying at least one fluid from a fluid line 51 to at least one of the reaction sites and a readout device 5. Readout device 5 may include means for locating a reaction site, such as the means for reading a locating mark at a reaction site and for monitoring the chemical assays or biochemical reactions at the reaction sites. Each of such fluid dispensers 50' includes a fluid dispenser outlet (not shown). Thus, the fluidics and detection functions of the apparatus may be combined in a multi-function head 4.

In FIG. 5, a perspective view of a third embodiment of the present invention, apparatus 1' includes a substrate 10 mounted on a rotary chuck 110 including a spindle 111. A rotary stepper motor (not shown) may rotate substrate 10 in either direction of arrow A'. A rail 14' is suspended above and transects, e.g., bisects substrate 10. A linear stepper motor 16', is mounted on rail 14', such that linear stepper motor 16' is movable in one dimension in the directions of arrow B' along rail 14' over the surface of substrate 10. Because stepper motors are used, a multi-function head may be moved to a particular reaction site and stopped and held at that site until a reaction is complete or for a predetermined period of time, i.e., a time sufficient to allow detection of assay results.

Rail 14' is mounted on a supporting arm 13. Supporting arm 13 may be mounted on a positioning motor (not shown), such that multi-function head 4 may be raised or lowered with respect to substrate 10.

Apparatus 1' may include substantially u-shaped platform 15' which may be suspended by four platform supports 17' from linear stepper motor 16'. A dispenser/readout support 115 is positioned within the open portion of u-shaped platform 15'. Fluid dispenser 50 including fluid supply line 51 and readouts device 5 including three optical fiber receptacles 52 and 54a and 54b and their associate optical fibers: read fiber 53 and tracking fibers 55a and 55b, are mounted on support 115.

Although fluid dispenser 50 and readout device 5 are initially positioned through the interaction of the movement of substrate 10 by the rotary stepper motor (not shown) and the movement of u-shaped platform 15' by linear stepper motor 16', adjustments to the position of fluid dispenser 50 and readout device 5 may be made by a three-axis micropositioner 56. Dispenser/readout support 115 maybe mounted on three-axis micropositioner 56, which may in turn be mounted on u-shaped platform 15'. Thus, micropositioner 56 may move dispenser/readout support 115 along three-axes to adjust the position of the fluid dispenser outlet (not shown) and optical fiber 53 and 55a and 55b.

The readout device 5 may be combined with a tracking system, such as in a (Compact Disc) CD pickup head, e.g., Sony KSS361A Optical Pickup manufactured by Sony Corporation of Tokyo, Japan, or the readout device 5 may be physically separate from the tracking system. In known optical pickup heads, such as those found in CD players, light emitted from a laser is split into three beams, i.e., a central and two flanking beams, and is directed onto the surface of the CD via a turning mirror and a lens. The central beam impinges upon the CD surface in order to read the binary coded information and to provide a feedback signal for focusing the central beam on the CD surface while the two flanking beams provide feedback signals for tracking the pickup head over the CD surface. The light reflected from the CD surface is received through the lens, is deflected by the turning mirror through the beam splitter, and impinges upon a photodiode array. Feedback signals then are generated by virtue of the geometry of the photodiode array. The operation of such feedback control systems is described in more detail in G. Thomas and W. Ophey, "Optical Recording," PHYSICS WORLD, 36–41 (December 1990), the disclosure of which is incorporated herein by reference.

The track pitch of a CD is about 1.6 microns and the width of the encoding pits on the CD surface is about 0.5 microns. The flanking beams described above, may strike the surface of the CD surface at a separation of about 2.1 microns apart, i.e., the CD track pitch plus the pit width. While a tracking system substantially similar to the CD tracking system described above may be suitable for the present invention, certain modifications may be necessary depending upon the precise configurations of the multi-function head and the substrate. In the present invention, for example, it may be necessary to alter the angle of separation of the flanking beams, so that they strike the CD surface at a wider or narrower separation to accommodate different sizes of reaction sites. This may be accomplished by altering or replacing the lens, as appropriate.

As noted above, the CD tracking system may employ a laser diode, which may emit primarily infrared light. The laser diode found in CD players typically emits a fraction of a milliwatt. Due to the nature of the assays performed with the present invention, the laser diode may be replaced with a fiber optic connector allowing a source of electromagnetic energy of a predetermined power and wavelength to be optically coupled to the apparatus. Moreover, a diffraction grating (not shown) may be placed in the path of the reflected beams. When such diffracted beams impinge upon a linear photodiode array, a spectrometer may be created. Such a spectrometer may be used to detect the progress or occurrence of a biological or chemical reaction at a reaction site.

In a preferred embodiment, the optics and the laser input of the CD tracking system may be modified to enable it to act as an excitation source and as a means for monitoring and reading the assay results at the reaction site, in addition to tracking the reaction sites. Referring to the foregoing description, the optics of the CD tracking system is altered to increase the separation between the three projected light beams, such that the two outer most beams straddle the well at a reaction site. The laser diode of the CD tracking system may then be replaced with a fiber optic connector to couple light in from any type of laser. Finally, the photodiodes in the photodiode array of the CD tracking system may be selectively replaced according to their sensitivity to wavelengths and low light levels that are expected to be received from the reaction sites. Alternatively, some or all of the photodiodes may be replaced with an appropriate photomultiplier tube.

As an alternative to this CD tracking system, readout device 5 may comprise three optical fibers, such as three fifty (50) micron fibers, arranged in a triangular configuration in the multi-function head 4. As depicted in FIG. 5, a first optical fiber receptacle 52 receives a first fiber 53. First optical fiber 53 may be split, e.g., bifurcated, such that first fiber 53 may function to deliver laser light to the substrate surface and to receive reflected light from the substrate surface. Consequently, first optical fiber 53 enables the apparatus to detect chemical and biochemical changes at the reaction sites and to read any indexing marks. The laser or light source is selected based on the type of assay(s) to be performed and is coupled to first fiber 53 by an optical fiber launcher, such as a KT210 Optical Fiber Launcher, manufactured by Thor Labs, Inc, of Newton, N.J., U.S.A. For example, first fiber 53 may be coupled to a photomultiplier tube (e.g., a photodiode array) or a spectrometer. Second and third optical fiber receptacles 54a and 54b receive a second fiber 55a and 55b, respectively. These two fibers 55a and 55b trail first fiber 53 and may be coupled to individual photodiodes to receive reflected electromagnetic energy and generate tracking signals.

Figure 6:
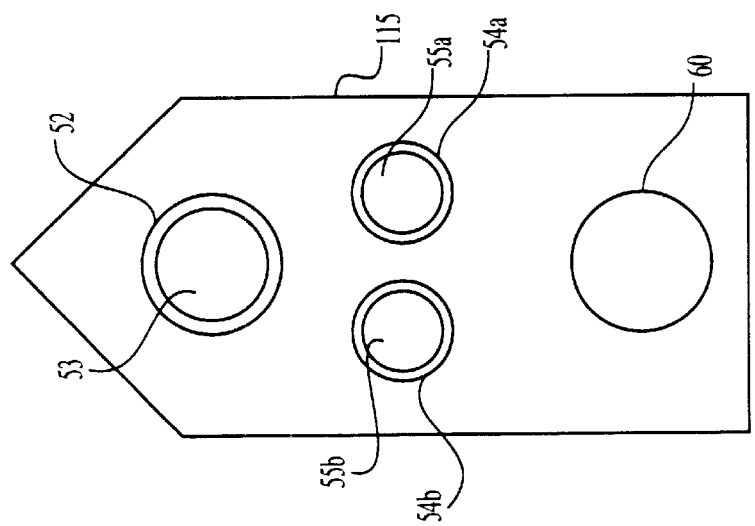
FIG. 6 is a bottom view of readout device depicting the configuration of the readout device including the arrangement of readout and tracking optical fibers.

Referring to FIG. 6, a bottom view of readout device 5 is depicted. This figure shows the arrangement of readout fiber 53 and tracking fibers 55a and 55b, with respect to the fluid dispenser outlet 60. In this alternative tracking system, an anti-reflective coating is applied in specific geometric configurations at precise locations along the substrate, such as that depicted in FIG. 7. Electromagnetic energy may be transmitted down the first or read fiber 53 and the second and third or tracking fibers 55a and 55b or down the read fiber exclusively. The modulation of the intensity of the reflected light by the anti-reflective coating may enable the indexing and tracking signals to be read.

Figure 7:
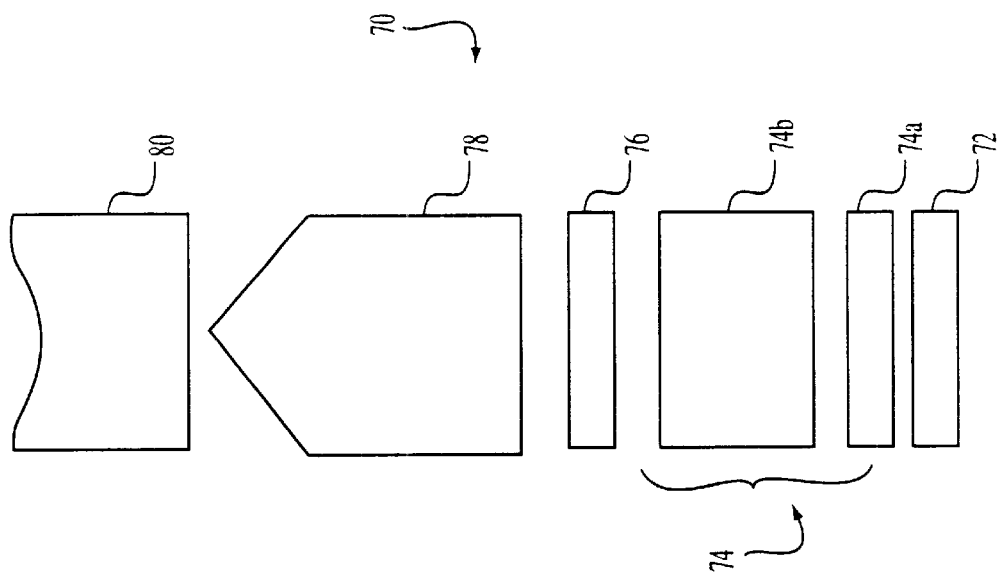
FIG. 7 depicts a locating mark combining tracking and indexing marks for guiding the multi-function head to the reaction site.

Referring to FIG. 7, a locating mark 70 may comprise both a start bit 72, an indexing mark 74, a dispense/stop bit 76, and a tracking bit 78. Start bit 72 instructs the readout device to begin reading the locating mark. Indexing mark 74 identifies the particular reaction site and may consist of one or more submarks, such as submarks 74a and 74b. Dispense/stop bit 76 may instruct multi-function head 4 to pause at theat position or to initiate the dispensing of an aliquot or aliquots for perform a chemical assay or to cause a biochemical reaction. Tracking mark 78 then guides the dispenser outlet (not shown) over a reaction site 80. As may be seen from a comparison of FIGS. 6 and 7, if multi-function head 4 is properly centered over locating mark 70, tracking fibers 55a and 55b receive an equal amount of reflected electromagnetic energy from the substrate surface. By analyzing a differential signal, shifts by multi-function head 4 or misalignment of the multi-function head 5 to the right or left may be detected, and these offsets may be corrected. For example, as depicted in FIG. 5, fluid dispenser 50 and redout device 5 comprising first, second and third fiber receptacles 52, 54a and 54b, respectively, may be mounted together on u-shaped platform 15' movably affixed to a three-axis micropositioner 56. Micropositioner 56 may permit further adjustments, e.g., in a range of less than about 15 mm with an accuracy of about one micron, in the position of fluid dispenser 50 and first, second and third fiber receptacles 52, 54a and 54b in three dimensions to improve the alignment of fluid dispenser outlet 60 or the read and tracking optical fibers or to adjust the focus of the electromagnetic energy reflected from the substrate surface. In addition, to determining the occurrence and progress of the reaction at the reaction site, read fiber 53 may scan the indexing mark. Read fiber 53 also may function as a proximity sensor to correct for movement by the multi-function head 4 away from or toward the substrate. This may be accomplished by monitoring the light intensity of the reflected light in areas in which the anti-reflective coating is absent.

Rough calibration may be necessary, and as a result, the entire multi-function head and feedback positioning system may be mounted on a XYZ translation stage that has a range of motion significantly greater than that of the fine-feedback positioning system that is mounted to the XYZ translation stage. Feedback actuation may be used to make fine adjustments to the positioning of the fluid dispenser and the readout device and may be provided by a variety of means, such as piezoelectric blocks, voice coils, worm drives, and the like. The apparatus may be modified to provide for such fine adjustments by the addition of a second three-axis micropositioner between the first micropositioner and the dispenser/readout support. This second micropositioner has a smaller range of movement and a higher degree of accuracy than the first micropositioner, e.g., a range of adjustment of less than about 100 microns and an accuracy of about 0.1 micron.

The shield structure also may comprise a cap formed over the geometric cavity of each reaction site. Such caps may include an opening sufficiently large to allow a stream of fluid to be directed therethrough, but sufficiently small, so as to retain the fluid within the cavity and reduce or eliminate evaporation of the fluid from the cavity. For example, streams containing nanoliter volumes of reagents, cleaning fluids, buffers, and the like, may be directed through the cap opening. A large volume droplet, e.g., a droplet having a volume in a range of about 0.1 to 0.5 $\mu$l, is then dispensed onto the cap opening. If the droplet has sufficient surface tension and is dispensed at a low velocity, it will seal the cap opening without entering the cavity. This sealing droplet may acts as a removable cover that may be removed by centrifugal force caused by the rotation of the substrate.

In addition, the sealing droplet may be electrically gated. By changing the electrical potential of the droplet through the use of appropriate electrodes and voltages, the wetting capabilities of the droplet may be altered to increase or decrease its adherence to the cap. Moreover, electronic components may be placed in the cavity to control the electrical gating of the covering drops.

Figure 8A:
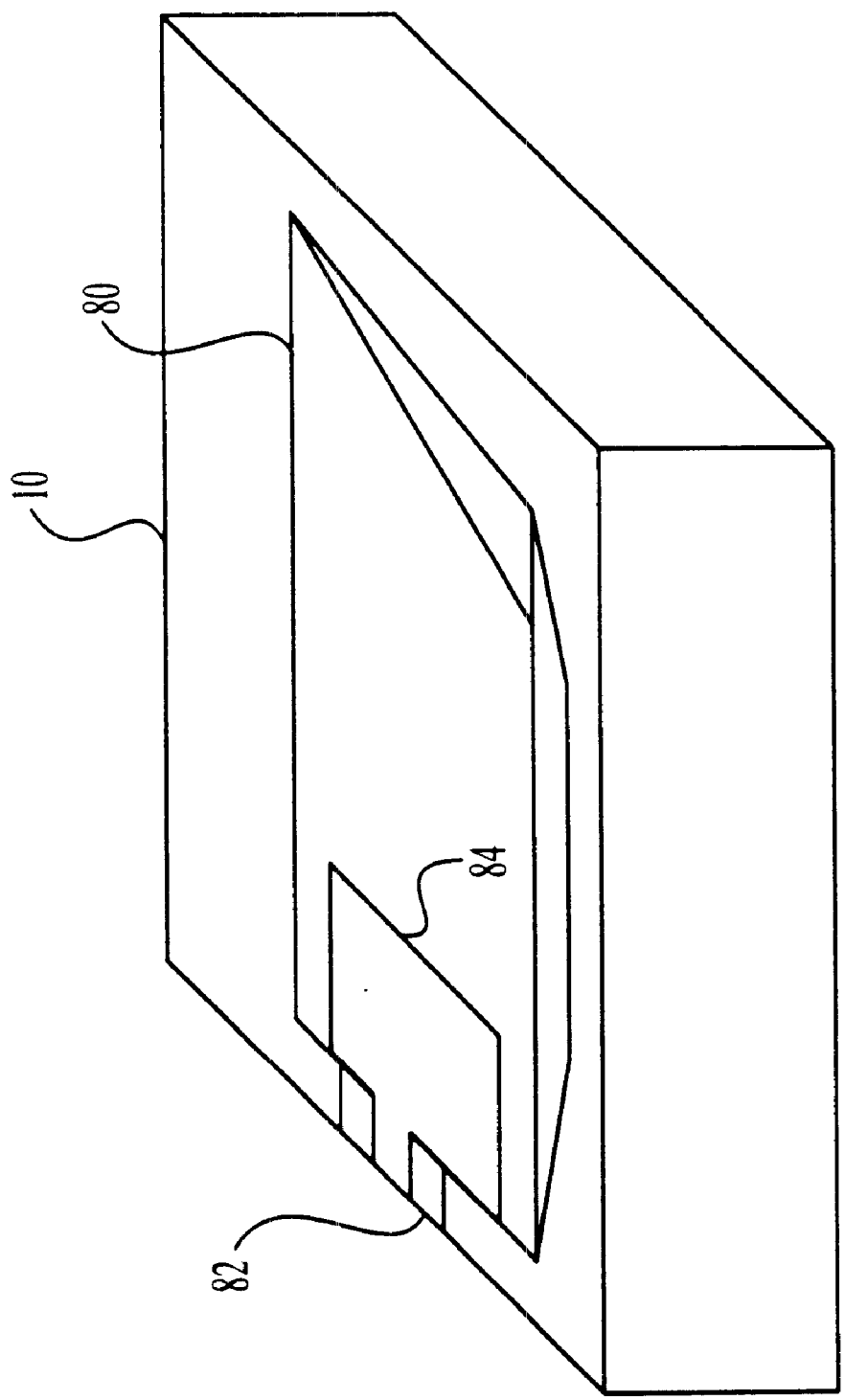
FIG. 8A depicts a perspective view of a reaction site on a substrate.
Figure 8B:
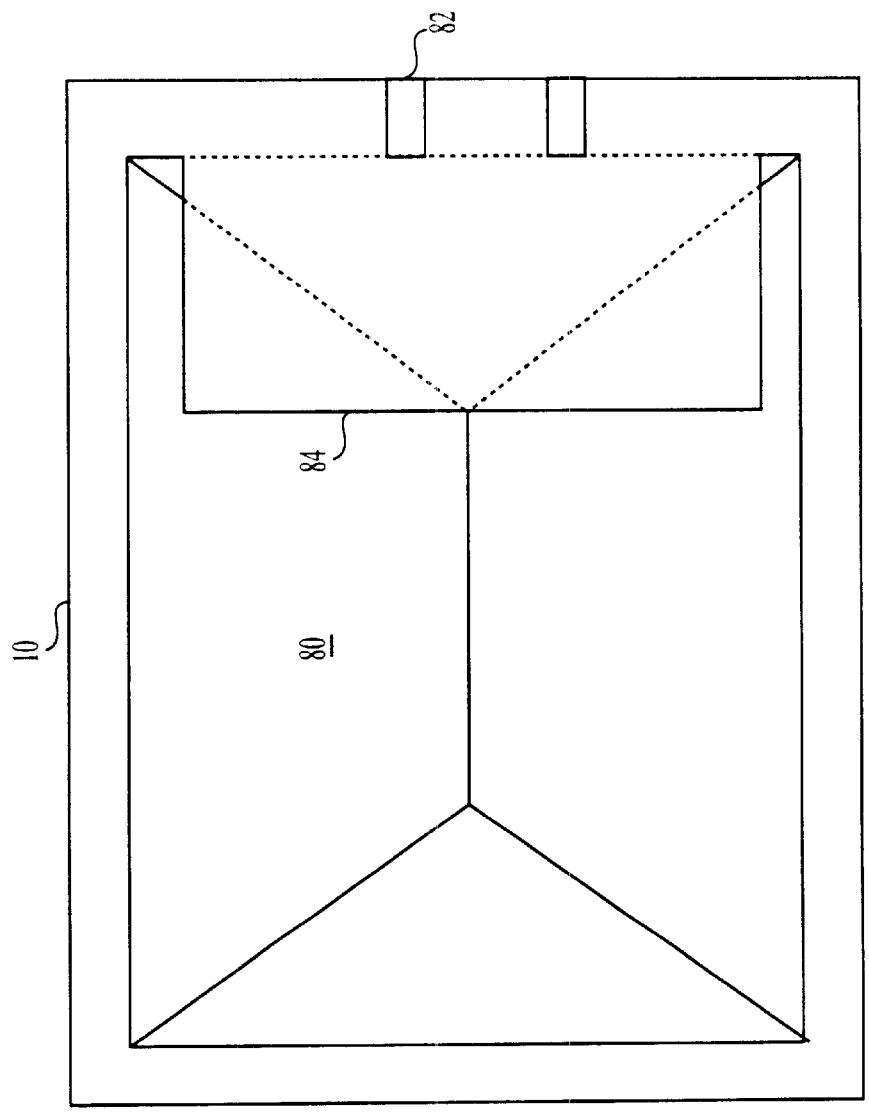
FIG. 8B depicts an overhead view of the reaction site of FIG. 8A.

Referring to FIGS. 8A and 8B, a reaction site 80 is depicted as a geometric cut or etched cavity formed in the surface of substrate 10. Reaction sites 80 may be formed by chemical etching or ion etching, or the like. Moreover, the shape of reaction site 80 may depend in part on the crystalline structure of substrate 10. Although the reaction site depicted in FIGS. 8A and 8B is shown to have a simple rectangular shape, it has a locating mark 82 and is equipped with a shield structure 84. Shield structure 84 aids in the reduction of evaporation losses from reaction site 80, the retention of fluid within reaction site 80, and the prevention fluid from covering locating mark 82. Surface micromachining, especially on semiconductor materials, is known in the art. Techniques for micromachining are discussed in K. Gabriel, *Engineering Microscopic Machines*, SCIENTIFIC AMERICAN, 150–53 (September 1995), which is incorporated herein by reference. Substrate 10 may include at least about 20,000 reaction sites, and preferably, at least about 100,000 reaction sites.

For example, a radial pattern comprising substantially square wells with edges with a length of about 110 microns may be formed in an oxide layer grown on a silicon wafer. A photo resist, such as a Microposit 1810 photoresist, manufactured by Shipley Company, Marlborough, Mass., U.S.A., may be spun onto the oxide layer on the surface of the silicon wafer. The photo resist may then be exposed through a mask to produce the appropriate pattern, and then developed and allowed to dry. The water then maybe placed in a hydrofluoric acid bath to remove the exposed oxide layer, and the wafer may be placed in a potassium oxide bath to etch the uncovered silicon. Acetone may be used to remove the residual photo resist, and a second hydrofluoric acid bath may be used to remove the remaining oxide. This procedure produces anisotropically etched wells with the geometric shape of an inverted pyramid.

Solid support substrates (not shown) may be formed within reaction sites 80. These structures provide a point at which biochemical probes may be affixed to the reaction sites 80. The probes may be used to bind particular targets such as polymers, e.g., polynucleotides, DNA, RNA, PNA, and antibodies, or antibody fragments or mixtures thereof In addition, the probes may bind targets such as individual nucleotides and nucleosides, such as adenosine, guanosine, cytosine, thymidine, uracil, or combinations thereof, and molecular structures such as enzymes proteins, plasmids, chromosomes and chromatids, and cellular structures, such as mitochondria, ribosomes, and the like. Moreover, microorganisms, such as prokaryotic or eukaryotic cells, including mammalian cells, bacteria, yeast and protozoa, viruses, phages, and combinations thereof, may be bound to the probes.

These structures may be formed by photolithographic techniques or materials may be incorporated into substrate 10 to form the solid support structures. For example, suitable materials which may provide points for direct probe attachment may include electrometal materials, such as gold, niobium oxide, iridium oxide, platinum, titanium, zinc, and other metals. Solid support substrates and probes may be used to ensure that particular targets are retained in particular reaction sites for testing. The use of such structures and probes is described in U.S. Pat. No. 5,532,128 to Eggers et al., which is incorporated herein by reference.

Locating marks 82 are discussed in detail with respect to FIG. 7 and may serve several functions. First, they allow the apparatus to determine its starting position. Second, they allow the apparatus to accurately deliver fluid to a predetermined reaction site by simply scanning the locating marks until the desired site is found. Third, although the precision achievable with the stepper motors may enable the apparatus to track its movements across the surface of substrate 10 by a form of dead-reckoning, the apparatus may detect positioning errors by comparing the apparatus's position by dead-reckoning to that of a known calibration point or reaction site. Fourth, because positioning errors may be determined, the apparatus may re-calibrate itself by comparing its calculated position to its known position with respect to the calibration points or reaction sites of substrate 10.

Figure 9C:
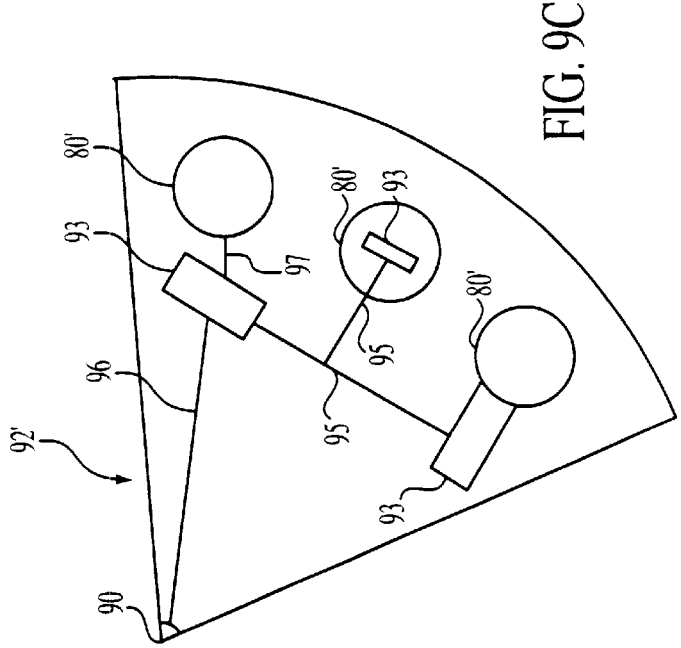
FIGS. 9B–9D depict overhead views of solid angle sectors of the substrate containing embodiments of reaction sites.
Figure 9A:
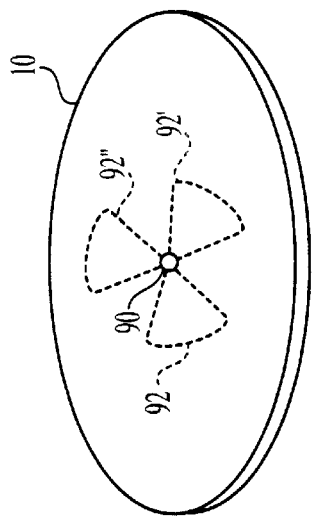
FIG. 9A depicts a perspective view of a substrate.
Figure 9B:
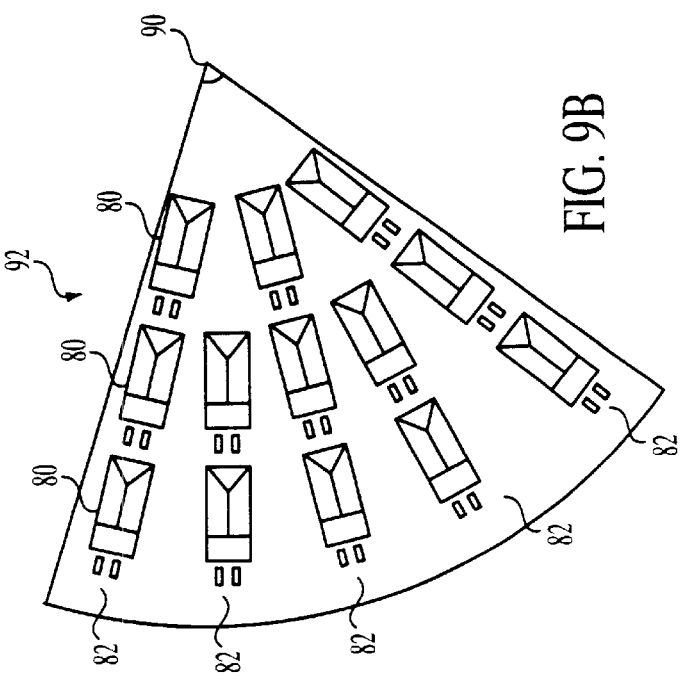
Figure 9D:
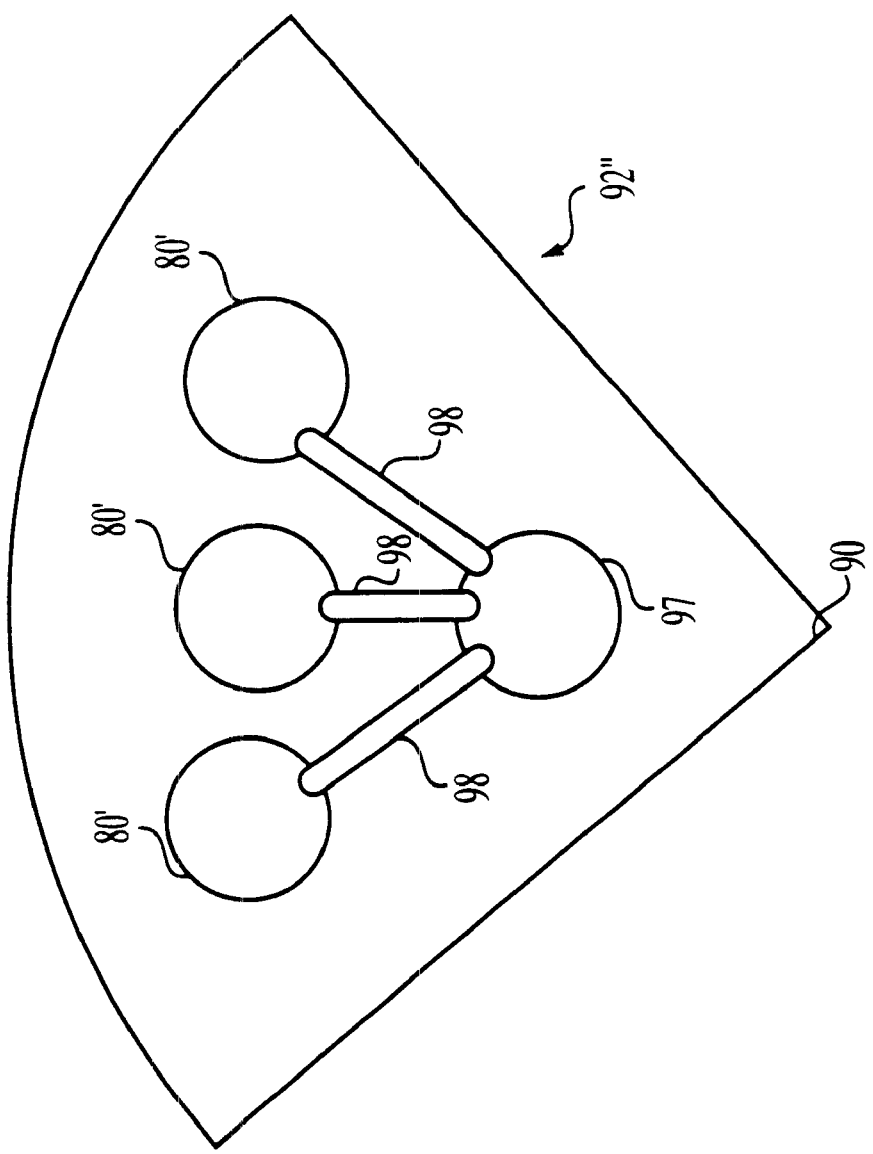

Referring to FIG. 9A, a perspective view of substrate 10 having a spindle 90 is depicted. Spindle 90 may support substrate 10 and permit the rotary stepper motor to engage substrate 10. Further, spindle 90 may permit electric connections between electronic and electromechanical elements, e.g., microelectromechanical systems, positioned on substrate 10 and power and control sources separate from substrate 10. FIGS. 9B–9D depict overhead views of solid angle sectors of substrate 10 exemplary of embodiments of substrate 10.

Referring to FIG. 9B, a solid angle sector 92 is shown, which includes a plurality of concentrically arranged non-interconnected reaction sites 80 aligned radially from spindle 60. Each of reaction sites 80 has locating mark 82, which is depicted as comprising two bars. The use of this identifying mark is intended to be merely exemplary, and other identifying marks, such as indexing marks, bar codes, number codes, color codes, or the like, may also be employed. Further, an identifying mark may consist of a combination of characters or markings, or both, and the position of the mark with respect to the center of substrate 10 or with respect to spindle 90.

Referring to FIG. 9C, a solid angle sector 92' is shown, which includes a plurality of circular reaction sites 80' and electronic or electro-mechanical elements 93, which are integral with, adjacent to, or connected to reaction sites 80'. Examples of such electronic elements include transponders for receiving and responding to an interrogation signal; heating coils for raising the temperature at a reaction site, temperature sensors to measure or monitor temperature or temperature changes at a reaction site; electric field generating elements for altering the electromagnetic field at a reaction site, e.g., to produce electrophoresis or to denature substances; photo-sensing elements for detecting light emissions caused by chemical or biochemical reactions at a reaction site or for detecting changes in the amount of light passing through substances as a result of a chemical or biochemical interaction; chemically sensitive gates, e.g., ChemFETS; ion sensitive gates, e.g., ISFETS; or a combination thereof. Further, a serpentine resistor may be used to heat proteins until denatured.

Generally, chemically sensitive gates and ion sensitive gates are transistors whose gates have been replaced with by an ion selective permeable membrane. Chemically and ion sensitive gates may be used to detect changes in pH as well as changes in chemical and ion composition. Further, substrate 10 may include interdigitated arrays (IDAs). An IDA may comprise two arrays of rectangular electrodes that are placed so that the arrays intermesh, but do not contact each other. Chemical reactions occurring between the arrays and generating electrical charges causes a resultant current to flow in the arrays. The resultant current flow may be monitored to indirectly monitor the progress of chemical reactions at the reaction site. Electro-mechanical elements 93 may produce a vibration at the reaction site to stir or mix a plurality of substances to facilitate or accelerate chemical or biochemical interactions.

In addition, substrate 10 may include elements, e.g., electrodes, that actively alter the electrostatic charge on substrate 10 in local areas. Such an electrostatic charge may attract or repel microvolumes of fluid. Consequently, such electrodes may be used to aid in delivering precise amounts of the at least one fluid to the at least one reaction site. With a plurality of controlled electrodes, an electrostatic field consisting of "hills" and "valleys" may be generated across the entire surface of substrate 10, thus, creating a plurality of "virtual" reaction sites. Generally, these electrostatic fields may be used to create vertical and horizontal containment fields. These virtual reaction sites may reduce cross-contamination between sites. The surface charge also may be manipulated by coating or depositing a material having a desired charge onto the surface of substrate 10. This technique may be used in conjunction with the elements described above.

Reaction sites 80' may be joined to elements 93 by a reaction site connection 64. As demonstrated by electronic or electromechanical elements 93 described above, connections 64 may transfer information concerning the reaction site or may serve to transfer energy to alter the chemical or biochemical interactions at the reaction site, or both. In addition, elements 93 may be connected to each other, e.g., interconnected, by axial connections 95 or by radial connections 96, or by a combination of these connections. Further, elements 93 may be interconnected radially through spindle 90, whereby signals may be transmitted to elements 93 from a computer (not shown) or other signal source and data from the reaction sites may be sent for storage and analysis to a computer or other data storage and analysis device or displayed on a monitor or printer or the like. Alternatively, elements may be interconnected via a device for combining two or more signals, i.e., a multiplexer (not shown). For example, by using a plurality of multiplexers with between about 10 to 100 connections per multiplexer, all of the reaction sites on the substrate may be interconnected.

Referring to FIG. 9D, a solid angle sector 92" is shown, which includes a plurality of circular reaction sites 80', a dispersion point 97, and a plurality of substantially radial channels 98, which channels 98 join dispersion point 97 to reaction sites 80'. In operation, dispenser outlet 21 may be aligned by rotary stepper motor 12 and linear stepper motor 16 with dispersion point 67. An amount of fluid then may be delivered to dispersion point 97. The rotary stepper motor may be used to rotate substrate 10 at sufficient speed to create a centrifugal force to draw a portion of the fluid from dispersion point 97 through channels 98 to reaction sites 80'.

As noted above, FIG. 9D depicts an embodiment using channels 98 and the centrifugal force generated by the rotation of substrate 10. However, it is not necessary to use such channels to transfer fluids to various reaction sites. If sufficient fluid is placed in a dispersion point 97 or in a plurality of dispersion points 97, the centrifugal force created by a rotating substrate 10 transfers a fluid across the entire surface of substrate 10 and to all reaction sites 80'. The amount of fluid required depends upon the size of the substrate, the number of reaction sites, the amount of fluid required at each reaction site, and the placement of the dispersion point or dispersion points.

Figure 10:
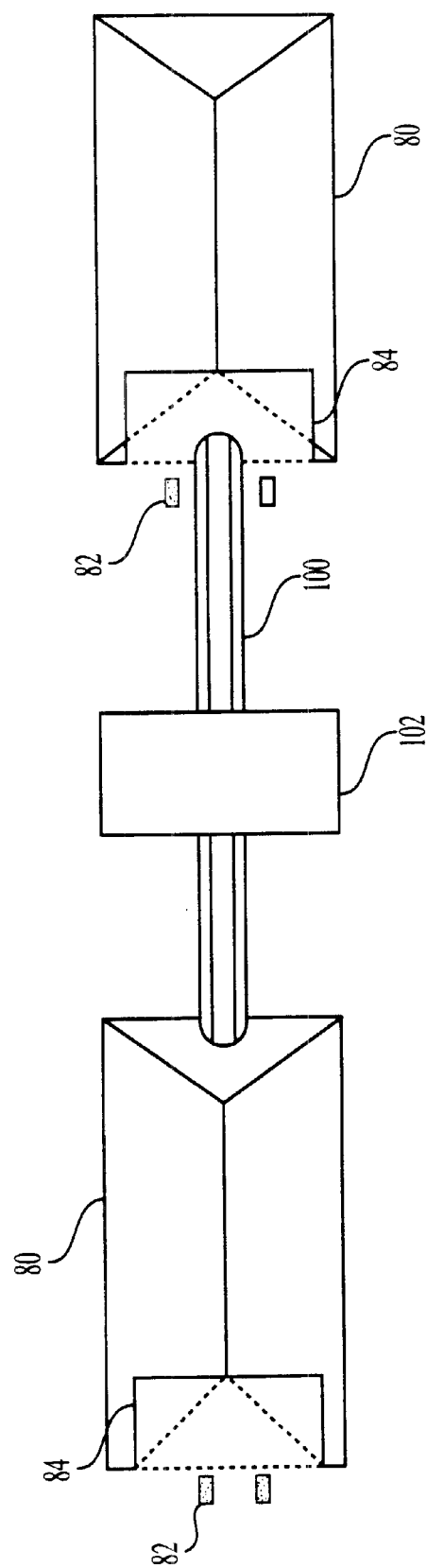
FIG. 10 depicts an overhead view of a pair of reactions sites joined by a channel and a microfluidic device.

FIG. 10 depicts an overhead view of a pair of reactions sites, i.e., reaction sites 80, joined by a channel 100 and a microfluidic device 102, such as a microfluidic pump or valve. Staged chemical and biochemical testing may be accomplished by providing a fluid or fluids to a reaction site for a first stage of testing and then the product or products of such first stage testing may be transferred by means of devices 102 through channels 100 to another reaction site or sites for subsequent testing stages. Channels 100 may be formed or etched or otherwise cut into the surface of substrate 10. Alternatively, channels 100 may be formed as tubes or conduits passing beneath the surface of substrate 10 to permit multi-level transfers of fluids or the products of chemical and biochemical reactions between reaction sites.

The invention may be more fully understood by consideration of the following examples and test results, which are intended to be purely exemplary of the invention and its operation and uses.

EXAMPLES AND TEST RESULTS

In a first example, the aliquots would be delivered to a dispenser outlet via a dispenser input tube. Aliquots and separating fluids, i.e., an immiscible fluid or a solvent, would pass through the dispenser input tube as a serialized fluid. Air gaps would be formed between each aliquots and each amount of separating fluid. The serialized fluid then would be delivered to the dispenser outlet at a pressure differential relative to the ambient pressure within container 18, e.g., a positive pressure in a range of about 0.01 to 2000 psi, and preferably, a positive pressure in a range of less than about 500 psi, such that the air gaps do not compress significantly. The movement of the aliquots may be monitored using a photo-diode and a photo-transmitter, which sense the change in the refractive index as the air gaps pass the sensor. The time between sensing and dispensing would be calculated based on the speed of the fluid flow.

The fluid flow may be dispensed continuously. However, a suction return tube would be positioned at the dispenser outlet, such that the suction return tube draws away the separating fluid portion of the fluid flow and leading and trailing portions of the aliquot. See FIG. 4C. The portion of fluid that is not drawn away, would be timed to flow straight from the dispenser outlet onto the surface of a silicon wafer. The suction device, which is connected to suction return tube, would be a high-vacuum system that is controlled via high-power solenoids located at a sufficient distance from the dispenser outlet, so that the forces do not cause shaking of the dispenser outlet in the vicinity of the silicon substrate. Thus, a continuous stream of fluid may be applied to cover everything, reaction sites and non-reaction sites, or individual aliquots may be delivered to individual reaction sites.

Once the reactions have occurred, the reaction results may be read. This would be accomplished by using a fiber optic tube that mounted adjacent to the dispenser outlet. The entire substrate surface then would be exposed to ultra-violet light. Reaction sites in which a blocking reaction occurred would show no fluorescence due to a fluorophor carried in the aliquot(s), e.g., conjugated with proteins contained in an aliquot. Other reaction sites would emit fluorescence. Preferably, however, the inverse situation would be employed, in which a researcher would determine the occurrence of a reaction by the presence, rather than absence, of the fluorescence.

An identifying mark, e.g., indexing marks and bar codes, may be placed adjacent to each reaction site, whereby a identifying mark reader would detect and read the mark by changes in its reflectance. Either ultra-violet or non-ultraviolet light may be used to determine the occurrence of a reaction, as well as to determine or verify the identity of a reaction site. Generally, reaction sites may be located via dead-reckoning. However, a dead-reckoning system would require periodic calibration. A feedback system, such as one utilizing identifying marks, may be used to confirm the accuracy of and, if necessary, re-calibrate a dead-reckoning system.

The following tests were conducted using samples consisting of Rhodamine 610 perchlorate dissolved in butanol at a concentration of about 2E-4 molar (hereinafter "Rhodamine solution"). Referring to the apparatus as depicted in FIGS. 5 and 6, a green He-Ne laser, lasing at about 543.5 nm, was used to transmit light along a first portion of a bifurcated optical fiber, e.g., optical fiber 53. The common end of this bifurcated fiber was oriented orthogonally to a silicon wafer (the substrate) mounted on a rotary chuck, such as rotary chuck 110 depicted in FIG. 5. The bifurcated optical fiber allows about 53 microwatts of laser light to impinge upon droplets of Rhodamine solution dispensed by a BioJet Quanti3000™ fluid dispenser. The portion of the laser light reflected from the substrate surface is gathered via the common end of the bifurcated fiber and transmitted along a second portion of the bifurcated optical fiber. The signal received by the second portion of the fiber is passed through a high pass filter in order to remove noise and feedback associated with the laser, at a cutoff wavelength of about 565 nm This filtered signal was then transmitted to a photomultiplier tube, (PMT) e.g., a Hamamatsu PMT, Model No. 5784-01, manufactured by Hamamatsu Corporation, of Bridgewater, N.J., U.S.A., for analysis.

Test 1

The purpose of this first test is (1) to determine whether the readout devices of the type intended for use in embodiments of this apparatus could actually detect the small volumes of a Rhodamine solution dispensed from the fluid dispensers suitable for use in the embodiments discussed above and (2) to determine the signal peak and the signal-to-noise ratio (SNR). The test involved the steps of: dispensing a droplet of Rhodamine solution having a volume of about 10.4 nl onto a silicon wafer and stepping the readout device across the droplet at a rate of about 1 mm/sec, while sampling the output of the PMT at a sampling rate of about 1000 Hz.

Figure 11:
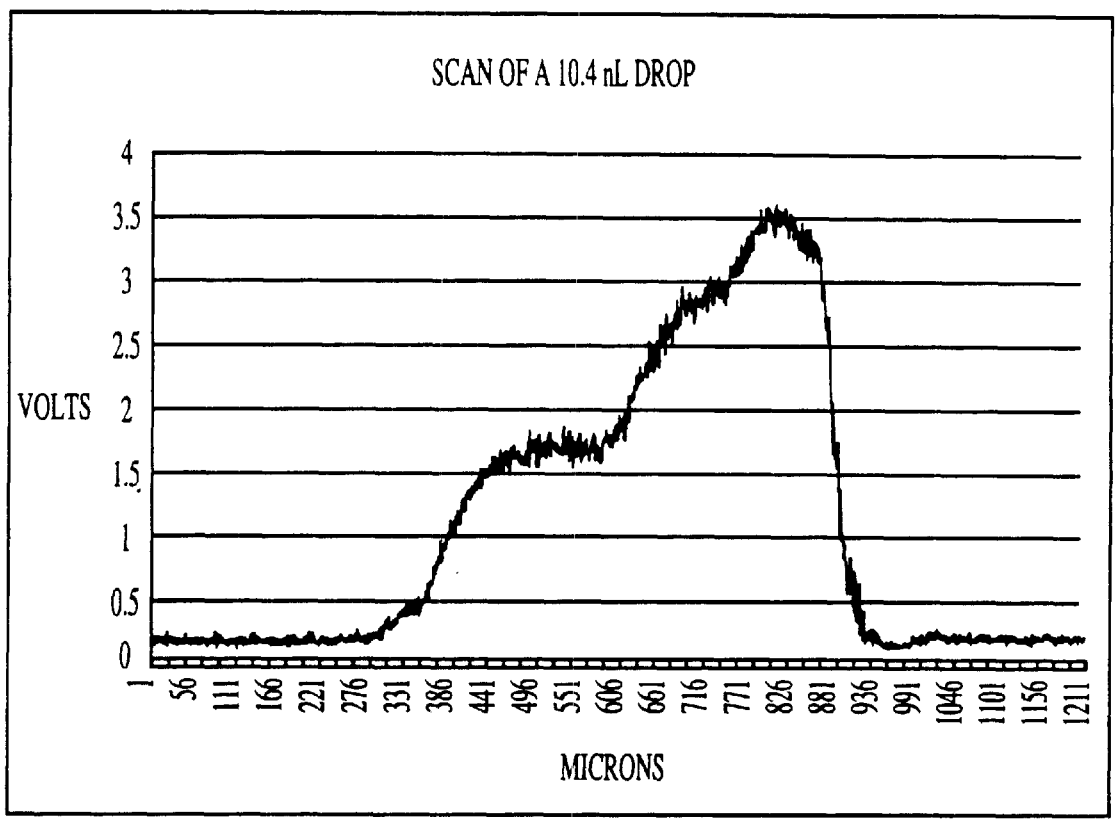
FIG. 11 is a graph of the laser detection scanning of a droplet of Rhodamine 610 solution deposited on a silicon substrate.

Referring to FIG. 11, the 10.4 nl droplet is clearly detectable. A peak output of about 3.5 V with a noise level of about 250 mV were measured. Thus, a SNR of about 14:1 was calculated using available fluid dispensing and readout devices. A significant portion of the signal noise could have been eliminated by using a bandpass filter centered on a wavelength of about 580 nm, i.e., the emission peak of the Rhodamine solution, instead of a highpass filter. Additionally, because the light exiting the fiber was not collimated, further signal degradation was experienced.

The approximate diameter of the droplet on the silicon wafer is determinable from the sampling data to be about 650 microns. However, a 10.4 nl sphere of fluid is calculated to have diameter of about 270 microns. Surface energy interactions between the droplet and the silicon wafer may cause the droplet of Rhodamine solution to spread out and coat the surface. Such spreading occurred in part because the droplets were placed on a flat surface of the silicon wafer, rather than into an etched well. As a result, the effective path length of light within the sample decreased, which weakened the resulting signal. Using appropriate geometry, i.e., wells, and appropriate surface coatings, it seems likely that the path length could be increased by at least a factor or two.

Test 2

The purpose of this second test was to create an intensity/thickness profile of a 10.4 nl droplet, to confirm the lower bounds of the dynamic range available for sensing, using available readout devices, and to determine source of hysteresis in the intensity signal. The test involved the steps of dispensing a droplet of Rhodamine solution having a volume of about 10.4 nl onto a silicon wafer and stepping the readout device forwards and backwards across the droplet at a rate of about 0.5 mm/sec, while sampling the output of the PMT at a sampling rate of about 500 Hz.

Figure 12A:
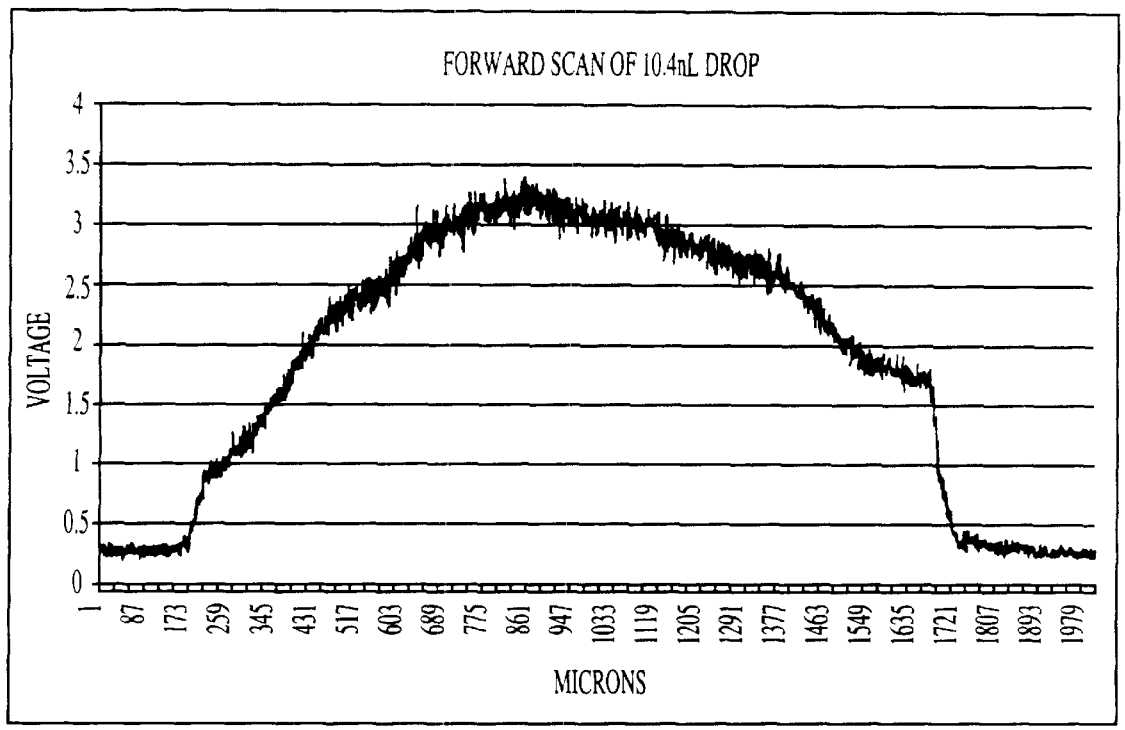
FIG. 12A is a graph of the forward laser size scanning of a droplet of Rhodamine 610 solution deposited on a silicon substrate.

The intensity plot of a droplet is primarily a function of two variables: the excitation path length, which is essentially the thickness of the drop, and the focusing effect created as light of the passes through the droplet. Because the tested droplets were relatively flat, the majority of the modulation of the intensity signal was primarily attributable to the thickness modulation across the droplet, rather than to any focusing effects. Consequently, the forward scan data depicted in FIG. 12A indicates that the excitation path length of the droplet (which is proportional to the thickness of the droplet) is greatest in the center of the droplet and least at the periphery of the droplet. This result was as expected. The left edge of the intensity profile indicated that a measurable signal was generated across a distance of about 85 microns. However, the right edge of the profile indicated that across a similar distance, the signal generated was about 1.5 times that of the left edge. This difference indicated that smaller areas of the droplet may be resolved if the path length were increased.

Figure 12B:
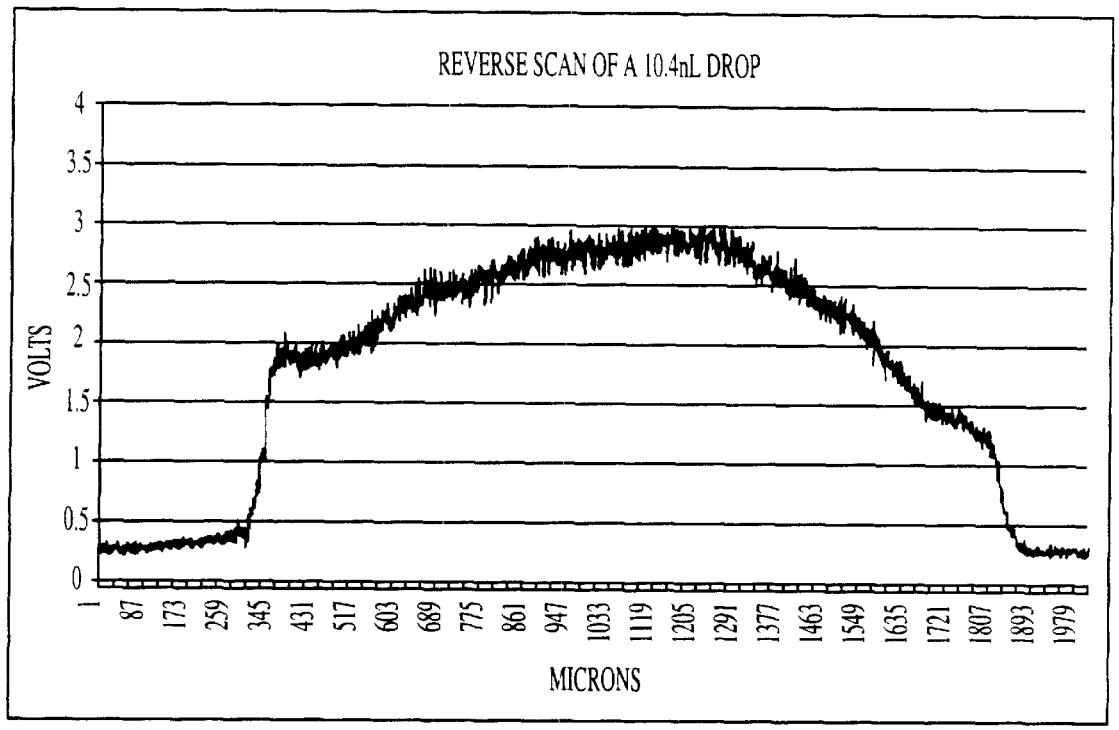
FIG. 12B is a graph of the reverse laser size scanning of a droplet of Rhodamine 610 solution deposited on a silicon substrate.

There was a distinct asymmetry in the forward scan intensity curve. Referring to FIG. 12B, the reverse scan intensity curve indicated that the source of hysteresis was the droplet itself The reverse intensity profile was a mirror image of the forward intensity profile. This suggested that the droplet sitting on the silicon wafer was "pushed" slightly to the right. The cause of this offset may be due to the fluid dynamics of the fluid dispenser, electrostatic effects, or a combination thereof. Moreover, the about one half-volt of signal lost on the reverse intensity curve was due to the evaporation of the droplet during testing.

Test 3

The purpose of this third test was to show open loop accuracy of the feedback stepper motors and to make a rough quantitative assessment of minimum detectable volume. The test involved the steps of dispensing a single droplet with a volume of about 10.4 nl in a known location and moving the readout device by dead-reckoning to the droplet, and monitoring the output of the PMT at a sampling rate of about 1000 Hz, until the droplet evaporated.

Figure 13:
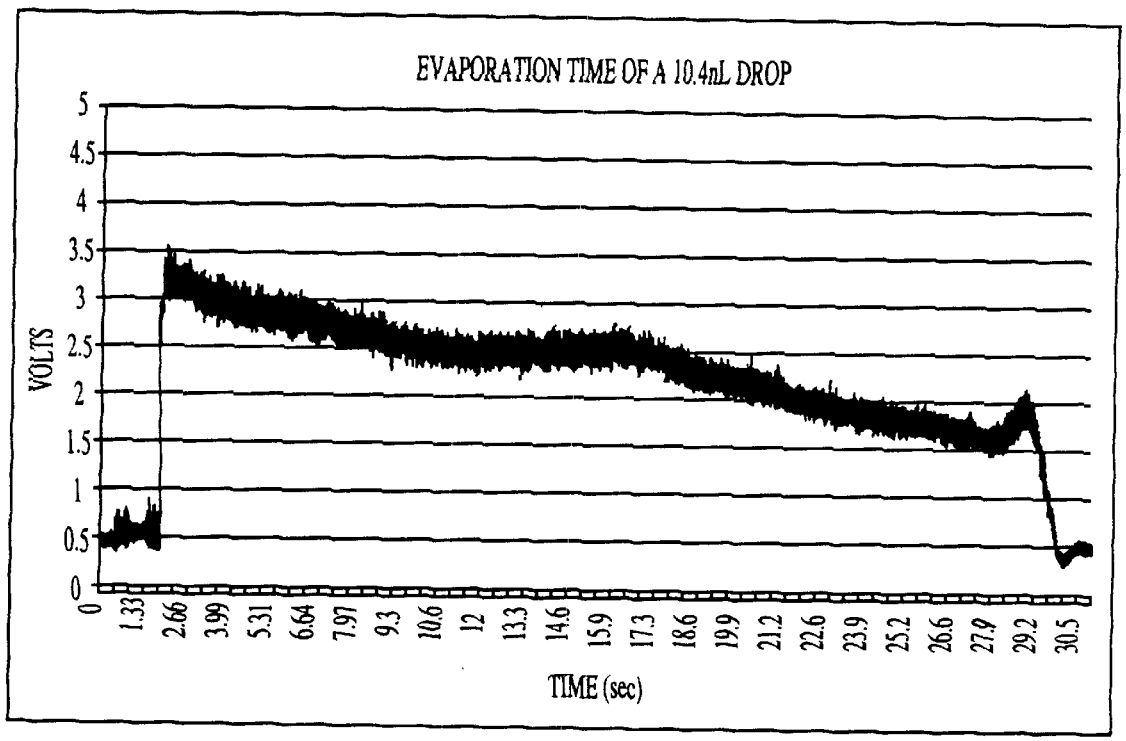
FIG. 13 is a graph of the showing the detectable volume of a droplet of Rhodamine 610 solution deposited on a silicon substrate and the effects of evaporation on the droplet volume over time.

Referring to FIG. 13, the accuracy of the operation and control of the stepper motor is evidenced by the intensity plot. The peak value of about 3.25 volts is similar to the peak values obtained in Test 1 when scanning a droplet. This indicates that the stepper motor and motor controls are capable of positioning a multi-function head substantially at the center of a droplet. Further, as discussed above, the three-axes micropositioner may be used to make adjustments, e.g., adjustments in a range of less than about 15 mm with an accuracy of about one micron, in any of three Cartesian axes to the position of the multi-function head, once the head has been positioned substantially over a reaction site.

As the volume of the droplet decreases due to evaporation, the intensity signal will decrease thereby tracking the loss of droplet volume. At some critical volume, which will depend in part on the initial droplet volume, the composition of the droplet, and the disposition of the droplet, e.g., on the flat substrate surface or in a geometric well, and the evaporation process accelerates significantly. Assuming that volume is linearly related to intensity and that the drop still has a volume of 10.4 nl when initially detected, by extrapolation, a volt signal may be correlated to a volume of about 3 nl. Consequently, a volume of about 3 nl may be a lower limit for the detection of a droplet using the equipment configuration of this test.

Nevertheless, other configurations may permit detection of still smaller volumes. These configurations may include modifications to the readout device's transmission and analysis of the interrogating light transmission, such as increasing the path length of the laser detection beam, using a bandpass filter to reduce or eliminate noise, collimating the light exiting the first portion of the bifurcated optical fiber, increasing the power of the excitation source, e.g., the laser, and combinations thereof. In addition, the structure of the substrate may be modified to improve detection capabilities, such as forming wells that are geometrically designed to reflect light back into the second portion of the bifurcated optical fiber, incorporating photodiodes at the base of each well, and the like. Finally, detection capabilities may be improved by systemic changes such as the reduction of coupling losses throughout the apparatus.

Test 4

The purpose of this fourth test was to demonstrate that a binary code could be successfully placed on the substrate and read by the readout device. The test involved the steps of depositing a 3-bit code that included a start and a stop bit on a silicon wafer at an annulus and subsequently, stepping the rotary stepper motor, such that the circumference of the annulus to be scanned passes under the bifurcated optical fiber. The resulting intensity signal was sampled at 1000 Hz. The binary code was formed from 0.1 microliter droplets of Rhodamine solution with the presence of a droplet indicating a one and the absence of a droplet indicating a zero. Each of the start and stop bits were indicated with a single droplet.

Figure 14:
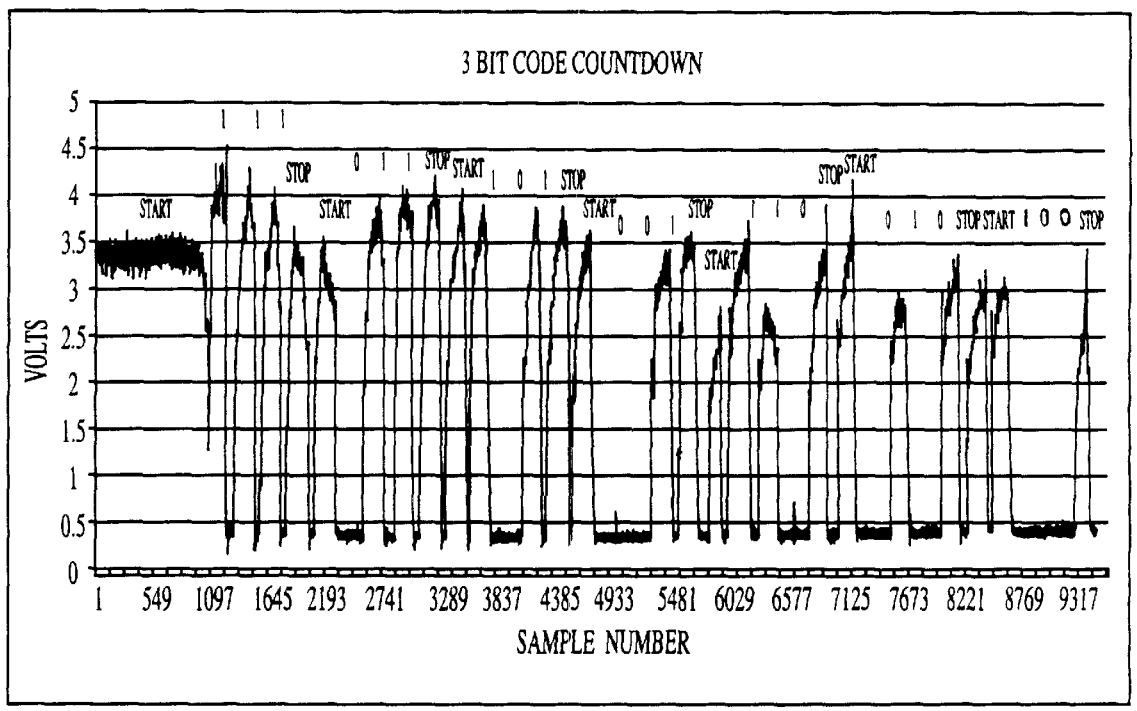
FIG. 14 is a graph showing the ability of the laser readout device to read a 3-bit code.

Referring to FIG. 14, the 3-bit code was successfully laid down and read back. The variation in pulse amplitude and duration were primarily due to evaporation of the droplets over the duration of the readout procedure. Generally, bits read later in the readout procedure generated lower signal intensity magnitudes. This indicates that a significant amount of evaporation occurred during the test. Nevertheless, the bit code remained readable even at the reduced droplet volumes.

Figure 15:
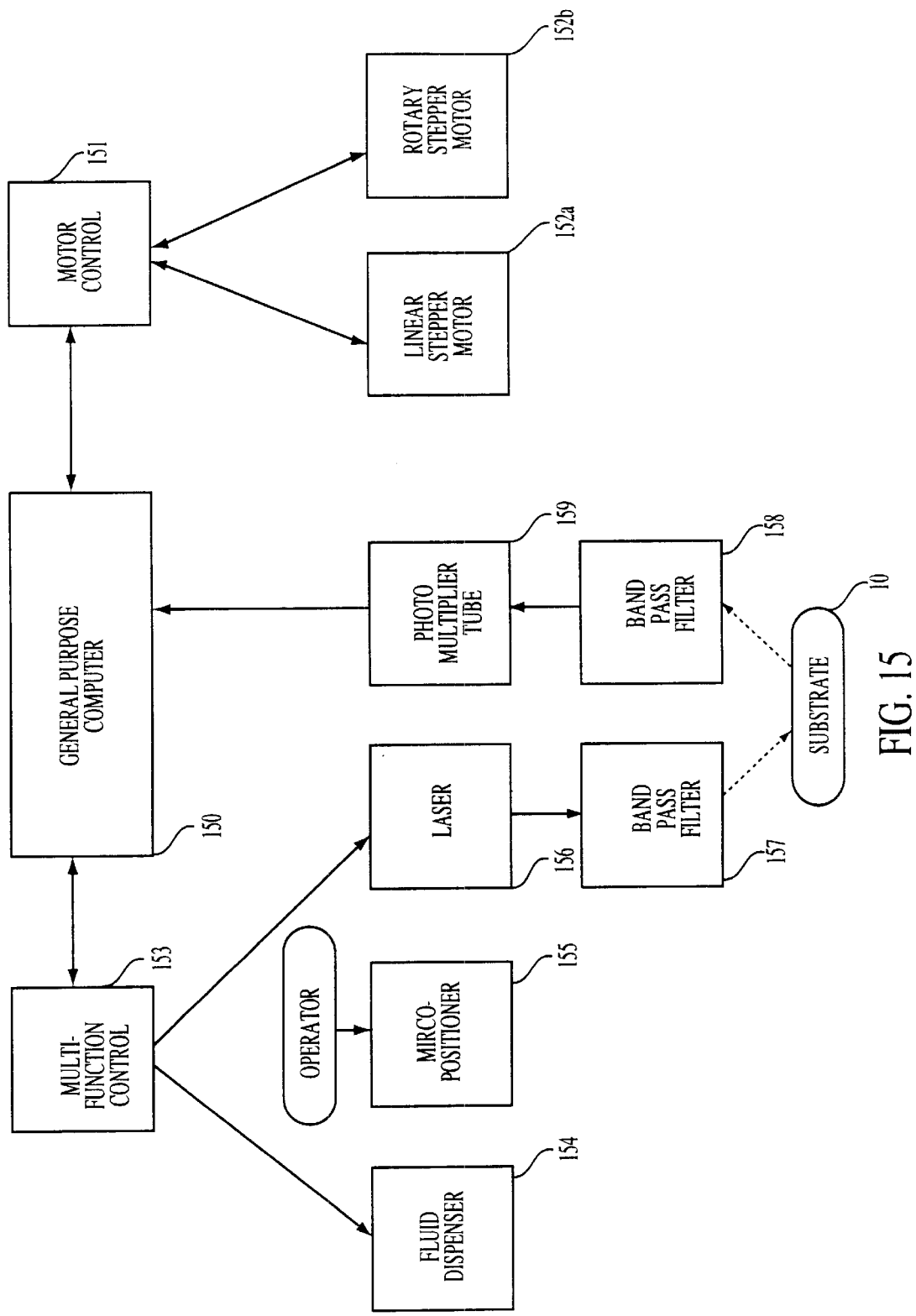
FIG. 15 is a schematic diagram depicting the apparatus.

Referring to FIG. 15, an second example describing the interface of the components of an embodiment of the apparatus having a multi-function head, is described. In this embodiment, overall control of the operation of the apparatus may be performed by a general purposed computer 150, such as a computer comprising a Pentium® II microprocessor, manufactured by Intel Corporation of Santa Clara, Calif., U.S.A., or the like, capable of operating at at least about 300 MHz. Moreover, computer 150 is preferably equipped with suitable software to create a coding environment fro accessing peripheral components. For example, suitable software includes LabVIEW®software, Part No. 776670-03, and the LabVIEW® PID Control Toolkit software, Part No. 7766634-11, which are commercially available from National Instruments, Inc., of Austin Tex., U.S.A.

Computer 150 is linked to a motor controller 151, e.g., an AT6200 Controller, manufactured by Parker Compumotor Company of Rohnert Park, Calif., U.S.A. Motor controller 151 relays instructions from computer 150 to a linear stepper motor 152a, e.g., a L20 Stepper Motor, manufactured by Parker Compumotor Company of Rohnert Park, Calif., U.S.A., and a rotary stepper motor 152b, e.g., a Zeta 57-51-10 Motor and a Zeta 4 Rotary Driver manufactured by Parker Compumotor Company of Rohnert Park, Calif., U.S.A., via motor control 151.

In addition, computer 150 may be linked to a multifunction control 153, e.g., a DAQ Board Model No. AT-MIO-16DE, manufactured by National Instruments, Inc., of Austin, Tex., U.S.A. A micropositioner 155, e.g., a Low-Profile Three-Axis Micropositioner, Part No. CR 4000, manufactured by the Daedal Division of Parker Compumotor Company of Rohnert Park, Calif., U.S.A., may be operated directly to make positioning adjustments in a range of less than about 15 mm with an accuracy of about one micron, along cartesian axes in the position of a fluid dispenser outlet and a readout device. Multi-function control 153 provides operating instructions received from computer 150 to at least a fluid dispenser 154, e.g., a BioJet Quanti3000™ fluid dispenser, manufactured by BioDot, Inc. of Irvin, Calif., U.S.A., and a laser 156. Laser 156 delivers a beam of light to the surface of a substrate 10, via a first bandpass filter 157. Laser 156 and first bandpass filter 157 are selected according to the assay to be accomplished. Further, light reflected from the substrate's surface then may pass through a second bandpass filter 158 to a photomultiplier tube 159, e.g., a Hamamatsu PMT, Model No. 5784-01, manufactured by Hamamatsu Corporation, of Bridgewater, N.J., U.S.A.

In this embodiment, fluid dispenser 154, micropositioner 155, and the readout device are combined on a multifunction head. Light from laser 156 is transmitted to the readout device over a fiber optic cable and from the end of the fiber optic cable is projected onto the surface of substrate 10. A suitable fiber optic cable for transmitting the light from laser 156 is a bifurcated cable, e.g., Bifurcated 50 $\mu$m Fiber Optic Cable, Part No. BIF50 UV/VIS, manufactured by Ocean Optics, Inc. of Dunedin, Fla., U.S.A. Such a cable allows a single cable to deliver laser light to the surface of substrate 10 and return it to photomultiplier tube 159.

As discussed above with respect to FIGS. 5 and 6, tracking fibers may be used to help align and guide the multi-function head to the reaction site. Such tracking fibers may be designed only to receive reflected light from the surface of substrate 10 which was generated by laser 156 and supplied by the bifurcated cable described above. Alternatively, the tracking fibers may also comprise bifurcated fiber optic cables and may provide their own light for tracking purposes. The light supplied to the tracking fibers may be generated by laser 156 or by a separate laser or lasers.

In one embodiment, each of the tracking fibers may comprise bifurcated cables and may supply light generated by laser 156 to the surface of substrate 10. Prior to the projection of the light from these tracking fibers onto the surface of substrate 10, the light transmitted by each fiber may pass through a separate bandpass filter, so that the light delivered by each tracking fiber is distinguishable over the light delivered by the other tracking fiber and over that delivered by the read fiber. As described above, with respect to the read fiber, in this embodiment, the reflected light gathered by the tracking fibers may also be filter again before it is returned to a photomultiplier or photo-diode array for analysis.

Other embodiments of the invention will be apparent to those skilled in the art from a consideration of this specification or practice of the invention disclosed herein. It is intended that the specification and these examples be considered as exemplary only. While the invention has been described in connection with preferred embodiments, it will be understood by those skilled in the art that other variations and modifications of these preferred embodiments described above can be made without departing from the scope of the invention.

We claim:

1. An apparatus for performing a plurality of assays, comprising:
    an axially rotatable substrate comprising a plurality of concentrically arranged, non-interconnected reaction sites;
    means for rotating and controlling the rotation of said substrate;
    a multi-function head comprising a fluid dispenser adapted to convey a fluid to said reaction sites, a fluid dispenser outlet, and a readout device;
    means for identifying at least one of said reaction sites; and
    means for aligning said multi-function head such that said fluid dispenser outlet may be aligned with at least one of said reaction sites.

2. The apparatus of claim 1, wherein said means for rotating is adapted to rotate and stop said substrate at an adjustable speed and controls the rotation of said substrate by adjusting said speed, acceleration, and a direction of rotation.

3. The apparatus of claim 1, wherein said means for rotating is controllable to rotate said substrate at speeds which creating a centrifugal force for removing a portion of said fluid from said reaction site.

4. The apparatus of claim 1, wherein said multi-function head includes a fluid dispenser movably mounted on a rail, said rail being oriented substantially parallel to a surface of said substrate, and wherein said means for aligning comprises a linear stepper motor for positioning said fluid dispenser along said rail such that said fluid dispenser outlet is directed toward said rotated substrate.

5. The apparatus of claim 4, wherein said rail transects said substrate.

6. The apparatus of claim 4, wherein said means for rotating comprises a rotary stepper motor.

7. The apparatus of claim 4, wherein said multi-function head is mounted on said linear stepper motor.

8. The apparatus of claim 4, wherein said means for identifying includes a sensor mounted on said multi-function head.

9. The apparatus of claim 8, wherein said sensor receives a signal emanating from said substrate.

10. The apparatus of claim 8, wherein said sensor transmits an interrogating signal and receives a locating signal.

11. The apparatus of claim 8, wherein said sensor reads a locating mark on said substrate's surface.

12. The apparatus of claim 8, wherein said sensor reads a locating mark on said substrate's surface.

13. The apparatus of claim 4, wherein said means for aligning comprises a computer having a memory for storing a start location on said substrate's surface for said multi-function head and said computer provides movement signals to said rotary stepper motor and linear stepper motor, whereby said motors align said multi-function head to allow said fluid dispenser to be substantially aligned over at least one of said reaction sites.

14. The apparatus of claim 1, wherein said multi-function head comprises a chemical reaction detection mechanism including an electromagnetic energy source and an electromagnetic energy receiver, whereby electromagnetic energy is directed into a first reaction site of said plurality of reaction sites by said source and electromagnetic energy generated in said first reaction site is received and analyzed to detect a chemical reaction or the products thereof by said receiver.

15. The apparatus of claim 14, wherein said electromagnetic energy source includes an optic fiber coupled to a light source, whereby light generated by said light source is directed into said at least one reaction site, and wherein said electromagnetic energy receiver includes a optic fiber functionally coupled to a photomultiplier having a bandpass filter, whereby an electrical signal is generated and transmitted to a computer to detect said chemical reaction.

16. The apparatus of claim 14, wherein at least one of said reaction sites is a geometric cavity formed in said substrate, said geometric cavity having a plurality of surfaces which are oriented to allow said electromagnetic energy to reflect within said cavity to increase an electromagnetic energy path length.

17. The apparatus according to claim 16, wherein reflective barriers are formed on a periphery of said cavity to prevent electromagnetic interference from an adjacent cavity.

18. The apparatus of claim 1, wherein said multi-function head comprises a chemical reaction detection mechanism including an electromagnetic energy receiver, whereby electromagnetic emission caused by chemical or biological reactions in at least one of said reaction sites are channeled to an electromagnetic energy detector for detection.

19. The apparatus of claim 1, wherein at least one of said reaction sites is a geometric cavity formed into said substrate.

20. The apparatus of claim 1, wherein said substrate is a manufactured from a material selected from the group consisting of glass, ceramics, semiconductor materials, plastics, composites, and combinations thereof.

21. The apparatus of claim 1, wherein said substrate includes solid support structures formed within said reaction sites which provide a plurality of points at which probes affix to said reaction sites.

22. The apparatus of claim 21, wherein said structures are formed from an electrometal material.

23. The apparatus of claim 1, wherein said fluid comprises discrete amounts of a fluid aliquot and a separating fluid, and said dispenser comprises a pump, a suction device adapted to draw a stream from said dispenser and a timing device for controlling said suction device, wherein said pump alternately draws a first discrete amount of said fluid aliquot and a second discrete amount of said separating fluid into a dispenser tube and delivers a serialized fluid of said fluid aliquot and said separating fluid to said dispenser under controlled pressure.

24. The apparatus of claim 23, wherein said timing device measures a flow rate of said stream through said dispenser tube and deactivates and subsequently reactivates said suction device to allow a portion of said first discrete amount of said fluid aliquot to be delivered to at least one of said reaction sites.

25. The apparatus of claim 24, wherein said flow sensor component is a plurality of magnetic beads and said flow senor is a magnetic sensor.

26. The apparatus of claim 23, wherein said first discrete amount of said fluid aliquot is substantially identical to said second discrete amount of said separating fluid, wherein said fluid aliquot includes a flow sensor component, and wherein said timing device includes a flow sensor for detecting said flow sensor component as said flow sensor component passes said sensor.

27. The apparatus of claim 1, wherein said fluid comprises a discrete amount of a fluid aliquot and of a separating fluid and said fluid dispenser comprises a pump, a valve mechanism, a suction device, and a timing device, wherein said pump draws a first discrete amount of said fluid aliquot and a second discrete amount of said separating fluid into a dispenser tube for delivering a serialized fluid of said fluid aliquot and said separating fluid to said dispenser under controlled pressure, a first portion of said serialized fluid is dispensed from said dispenser to at least one of said reaction sites said suction device removes an unwanted portion of said first portion of said serialized fluid, and said timing device controls said valve mechanism and said suction device.

28. The apparatus of claim 27, wherein said dispenser extends substantially perpendicular to a direction of fluid flow within said dispenser tube and said valve mechanism comprises a controller and a valve controlled by said controller, said value being positioned downstream from said dispenser and said controller being controlled by said timing device, such that when said valve is closed, said fluid flows to said dispenser outlet.

29. The apparatus of claim 1, further comprising a valve mechanism comprising a controller and a valve controlled by said controller, said valve for controlling fluid flow from said dispenser, wherein said dispenser extends substantially perpendicular to a direction of fluid flow within said dispenser tube, and wherein said valve being positioned downstream from said dispenser and said controller is controlled by a timing device such that when said valve is closed, said fluid flows to said dispenser outlet.

30. The apparatus of claim 29, wherein said timing device measures a flow rate of said fluid flow through said dispenser tube.

31. The apparatus of claim 29, wherein said valve mechanism comprises
a four-way valve in said dispenser tube;
a first controller and a first valve controlled by said first controller, said first valve being positioned downstream from said four-way connection;
a second controller and a second valve controlled by said second controller, said second valve being positioned upstream from said four-way connection, and wherein said dispenser extends from a first orifice of said four way connection such that said first controller and said second controller are controlled by said timing device and when said first and said second valves are closed, a dispenser fluid is pumped through said four-way connection and forces said fluid to said disperser outlet.

32. The apparatus of claim 1, wherein said fluid dispenser ejects a micro-droplet stream of said fluid from said dispenser and an electrostatic accelerator and deflector directs said micro-droplet stream to at least one of said reaction sites.

33. The apparatus of claim 1, wherein said means for identifying includes a light source and a florescence detector and wherein a plurality of said fluid aliquot is delivered to said reaction sites, and wherein said fluid includes a flourophor, whereby florescence occurs in at least one of said reaction sites.

34. The apparatus of claim 1, wherein said substrate comprises a plurality of layers of a semiconductor material, and wherein an electronic element is formed on said semiconductor material and jointed to at least one of said reaction sites.

35. The apparatus of claim 34, wherein said at least one electronic element is selected from the group consisting of transponders, heating coils, temperature sensors, electric field generating elements, photosensing elements, electrophoresing elements, denaturing elements, chemically sensitive gates, ion sensitive gates, interdigitated arrays, and combinations thereof.

36. The apparatus of claim 34, wherein said electronic element comprises a plurality of interconnected electronic elements.

37. The apparatus of claim 36, further comprising a spindle around which said substrate rotates and wherein a pair of said electronic elements are radially interconnected through said spindle.

38. The apparatus of claim 36, wherein said pair of electronic elements are axially interconnected.

39. The apparatus of claim 36, further comprising a multiplexor for interconnecting said electronic elements.

40. The apparatus of claim 1, further comprising a electromechanical element that is formed on said substrate adjacent at least one of said reaction sites.

41. The apparatus of claim 40, wherein said electromechanical element produces a vibration to agitate said fluid within at least one of said reaction sites.

42. The apparatus of claim 1, wherein said means for rotating comprises a first rotary stepper motor, and wherein said dispenser outlet is mounted on a pivot arm and said pivot arm is mounted on a secondary stepper motor, such that said dispenser outlet is pivotably controllable over said rotatable substrate.

43. The apparatus of claim 1, wherein said substrate and said fluid dispenser are enclosed within an air-tight container.

44. The apparatus of claim 1, wherein at least one of said reaction sites comprises a geometric cavity formed in said substrate, said geometric cavity having a shield structure to prevent fluid loss from said reaction site.

45. The apparatus of claim 44, further comprising a pressure control device for controlling atmospheric pressure within said container.

46. The apparatus of claim 1, wherein said multi-functional head comprises a plurality of fluid dispensers.

47. The apparatus of claim 1, wherein said apparatus includes at least about 20,000 radially arrayed reaction sites.

48. The apparatus of claim 1, wherein said fluid dispenser is adapted to convey an amount less than about 0.5 $\mu$l of said fluid to each of said reaction sites.

49. An apparatus for performing a plurality of assays comprising:
an axially rotatable substrate comprising a plurality of concentrically arranged non-interconnected reaction sites;
means for rotating said substrate;
a multi-function head including a fluid dispenser adapted to convey a fluid to each said reaction sites, a fluid dispenser outlet, and a readout device;
means for identifying at least one of said reaction sites; and
means for aligning said multi-function head such that said fluid dispenser outlet is substantially aligned with at least one of said reaction sites, wherein said means for rotating is controllable to rotate said substrate at a speed to allow a portion of said fluid be removable from at least one of said reaction sites by a centrifugal force generated by the rotation of said substrate.

50. The apparatus of claim 49, wherein said multi-functional head comprises a plurality of fluid dispensers.

51. The apparatus of claim 49, wherein said apparatus includes at least about 20,000 radially arrayed reaction sites.

52. The apparatus of claim 49, wherein said fluid dispenser is adapted to convey an amount less than about 0.5 $\mu$l of said fluid to each of said reaction sites.

* * * * *